(12) United States Patent
Appel et al.

(10) Patent No.: US 11,154,521 B2
(45) Date of Patent: *Oct. 26, 2021

(54) PALATABLE COMPOSITIONS INCLUDING SODIUM PHENYLBUTYRATE AND USES THEREOF

(71) Applicant: Acer Therapeutics Inc., Newton, MA (US)

(72) Inventors: Leah E. Appel, Bend, OR (US); Joshua R. Shockey, Bend, OR (US); D. Christopher Schelling, Bend, OR (US)

(73) Assignee: Acer Therapeutics Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/196,416

(22) Filed: Mar. 9, 2021

(65) Prior Publication Data

US 2021/0186908 A1    Jun. 24, 2021

Related U.S. Application Data

(63) Continuation of application No. 16/746,186, filed on Jan. 17, 2020, which is a continuation of application No. 15/295,881, filed on Oct. 17, 2016, now abandoned.

(60) Provisional application No. 62/308,614, filed on Mar. 15, 2016.

(51) Int. Cl.
*A61K 31/192* (2006.01)
*A61K 9/50* (2006.01)
*A61K 47/32* (2006.01)

(52) U.S. Cl.
CPC .......... *A61K 31/192* (2013.01); *A61K 9/5078* (2013.01); *A61K 9/5089* (2013.01); *A61K 47/32* (2013.01); *A61K 9/5026* (2013.01)

(58) Field of Classification Search
None
See application file for complete search history.

(56) References Cited

U.S. PATENT DOCUMENTS

| | | |
|---|---|---|
| 6,984,403 B2 | 1/2006 | Hagen et al. |
| 2004/0152784 A1 | 8/2004 | March |
| 2007/0196483 A1 | 8/2007 | Appel et al. |
| 2011/0027251 A1 | 2/2011 | Frechilla Manso et al. |
| 2012/0220661 A1 | 8/2012 | Lee |
| 2014/0178484 A1 | 6/2014 | Zala et al. |

(Continued)

FOREIGN PATENT DOCUMENTS

| | | |
|---|---|---|
| EP | 2389932 A1 | 11/2011 |
| EP | 2599477 A1 | 6/2013 |

(Continued)

OTHER PUBLICATIONS

U.S. Appl. No. 17/196,599, Appel et al.

(Continued)

*Primary Examiner* — Isis A Ghali
(74) *Attorney, Agent, or Firm* — Clark & Elbing LLP

(57) ABSTRACT

The present invention features palatable pharmaceutical compositions including sodium phenylbutyrate and methods for the treatment of inborn errors of metabolism (e.g., Maple Syrup Urine Disease or Urea Cycle Disorders), neurodegenerative disorders such as Parkinson's disease, spinal muscular atrophy, dystonia, or inclusion-body myositis with such compositions.

27 Claims, 8 Drawing Sheets

(56) References Cited

U.S. PATENT DOCUMENTS

| | | |
|---|---|---|
| 2014/0187638 A1 | 7/2014 | Marin |
| 2014/0227351 A1 | 8/2014 | Folger et al. |
| 2015/0024048 A1 | 1/2015 | Hemmingsen et al. |
| 2020/0261385 A1 | 8/2020 | Appel et al. |

FOREIGN PATENT DOCUMENTS

| | | |
|---|---|---|
| FR | 2959129 B1 | 2/2013 |
| JP | 2007-525413 A | 9/2007 |
| JP | 2014-521713 A | 8/2014 |
| JP | 2015-533164 A | 11/2015 |
| JP | 2016-006025 A | 1/2016 |
| WO | WO-2004/066925 A2 | 8/2004 |
| WO | WO-2011/011781 A1 | 1/2011 |
| WO | WO-2012/077038 A1 | 6/2012 |
| WO | WO-2012/168882 A1 | 12/2012 |
| WO | WO-2013/024023 A1 | 2/2013 |
| WO | WO-2014/062446 A1 | 4/2014 |
| WO | WO-2014/114255 A2 | 7/2014 |

OTHER PUBLICATIONS

"VIVAPHARM® HPMC," JRS Pharma, http://www.jrspharma.com/pharma_en/products-services/coatings/vivapharm-hpmc/, retrieved on Oct. 11, 2017 (2 pages).

Common Drug Review, "Clinical Review Report," (2016).

Dover et al., "Induction of fetal hemoglobin production in subjects with sickle cell anemia by oral sodium phenylbutyrate." Blood. 84(1): 339-343 (1994).

European Medicines Agency (EMA), "Summary of product characteristics: Pheburane.".

Extended European Search Report for European Patent Application No. 16894786.9, dated Oct. 4, 2019 (10 pages).

Guffon et al., "Developing a new formulation of sodium phenylbutyrate," Arch Dis Child. 97(12):1081-5 (2012).

Haute Autorité de Santé, Transparency Committee Opinion (English Translation) (2014).

Häberle et al., "Suggested guidelines for the diagnosis and management of urea cycle disorders." Orphanet J Rare Dis. 7: 32 (2012).

International Search Report and Written Opinion for International Application No. PCT/US16/57415, dated Jan. 10, 2017 (13 pages).

Kibleur et al., "Results from a nationwide cohort temporary utilization authorization (ATU) survey of patients in France treated with Pheburane (Sodium Phenylbutyrate) taste-masked granules," Paediatr Drugs. 16(5): 407-415 (2014).

Koren et al., "Averting the foul taste of pediatric medicines improves adherence and can be lifesaving—Pheburane® (sodium phenylbutyrate)," Patient Prefer Adherence. 10: 2141-2144 (2016).

Longo et al., "Glycerol phenylbutyrate for the maintenance treatment of patients with deficiencies in enzymes of the urea cycle." Expert Opinion on Orphan Drugs. 5(12): 999-1010 (2017).

Mew et al., "Urea cycle disorders overview." GeneReviews. Seattle, Washington: University of Washington, Seattle (1993).

Nagamani et al., "Self-reported treatment-associated symptoms among patients with urea cycle disorders participating in glycerol phenylbutyrate clinical trials," Mol Genet Metab. 116(1-2): 29-34 (2015).

Nakano et al., "Effect of food on the pharmacokinetics and therapeutic efficacy of 4-phenylbutyrate in progressive familial intrahepatic cholestasis," Sci Rep. 9(1): 17075 (2019) (12 pages).

Peña-Quintana et al., "Profile of sodium phenylbutyrate granules for the treatment of urea-cycle disorders: patient perspectives." Patient Prefer Adherence. 11: 1489-1496 (2017).

Pheburane Assessment Report (2013).

Prescribe International, "Sodium phenylbutyrate coated granules (Pheburane). Defective urea synthesis: a welcome formulation," Prescrire Int. 24(157): 35-36 (2015).

Shchelochkov et al., "Barriers to drug adherence in the treatment of urea cycle disorders: Assessment of patient, caregiver and provider perspectives," Mol Genet Metab Rep. 20 (8):43-7 (2016).

Ucar et al., "One year experience of Pheburane (Sodium Phenylbutyrate) treatment in a patient with Argininosuccinate Lyase deficiency," JIMD Rep. 19:31-3 (2015).

PE Pharma Excipients Eudragit E PO, downloaded Jun. 14, 2021 (Year: 2021).

Ashland, Benece HPMC, downloaded Jun. 15, 2021 (Year: 2021).

PALATABLE COMPOSITIONS INCLUDING SODIUM PHENYLBUTYRATE AND USES THEREOF

BACKGROUND OF THE INVENTION

Inborn errors of metabolism are a class of disorders arising from congenital disorders of metabolism. Many of the disorders are the result of defects of single genes that code for enzymes important for metabolism of certain substrates. The reduced activity of the enzymes results in accumulation of substrate to toxic levels which, in turn, leads to various symptoms depending on the substrate.

Deregulation of branched chain amino acid catabolism leads to an inborn error of metabolism known as maple syrup urine disease (MSUD). MSUD, also referred to as Branched-Chain Keto Aciduria, is an autosomal recessive disorder, typically diagnosed within 4-7 days after birth, with an incidence of approximately 1 in 185,000 live births. MSUD is caused by mutations that result in a deficiency in the mitochondrial branched-chain ketoacid dehydrogenase complex (BCKDC), resulting in the accumulation of the BCAAs (leucine, valine, isoleucine) and their corresponding α-keto acids (BCKAs) (α-ketoisocaproate, α-ketoisovalerate, and α-keto-β-methylvalarate) in cells and body fluids in MSUD patients. As described in International Patent Publication No. WO2011011781, herein incorporated by reference, sodium phenylbutyrate is useful in the treatment of MSUD. If left untreated MSUD patients develop high BCAA levels and suffer from chronic and acute neurological damage, including low IQ, mental impairment (poor cognitive function), social impairment (poor executive function), and metabolic decompensation (seizures and coma), central respiratory failure, and death may follow.

Urea cycle disorder (UCD) is another disorder arising from an inborn error of metabolism, with an approximate incidence of 1 in 30,000 births and are characterized by the accumulation of toxic levels of nitrogen as ammonia and glutamate in the blood. In UCD, a mutation causes a deficiency in an enzyme of the urea acid cycle (for example N-acetylglutamate synthetase, carbamoyl phosphate synthetase I, ornithine transcarbamylase, argininosuccinic acid sythetase, argininosuccinic acid lyase, or arginase) and can result in life-threatening neurological complications. Treatment with phenylacetic acid (PA), or its pro-drug phenylbutyrate (PB), removes excess nitrogen from the system as PA is acetylated to phenylacetylglutamine and excreted through the kidneys. An immediate release formulation of sodium phenylbutyrate (BUPHENYL®) has been approved for the treatment of UCD, and a modified release form of phenylbutyrate (RAVICTI®) has also been approved for the treatment of UCD.

Neuroinflammation and oxidative stress are underlying causes of various neurodegenerative disorders such as Parkinson's disease. Sodium phenylbutyrate has been shown to suppress both proinflammatory molecules and reactive oxygen species (ROS) in activated glial cells indicating that it may be useful for the treatment of neurodegenerative disorders such as Parkinson's disease.

Spinal muscular atrophy (SMA) is an autosomal recessive neuromuscular disease, characterized by degeneration of the anterior horn cells of the spinal cord. All forms of SMA are caused by homozygous loss of the functional survival motor neuron (SMN1) gene resulting in insufficient levels of the SMN protein. Sodium phenylbutyrate has been found to be effective in enhancing SMN protein levels and the number of SMN-containing nuclear structures. Accordingly, sodium phenylbutyrate may be effective for the treatment of SMA.

Dystonia is a neurological disorder involving sustained muscle contractions. Early-onset primary dystonia is the most common form of hereditary dystonia and is caused by deletion of a glutamic acid residue near the carboxyl-terminus of torsinA. Mutation in torsinA has been found to induce ER stress, and inhibit the cyclic adenosine-3',5'-monophosphate (cAMP) response to the adenylate cyclase agonist forskolin. As described in Cho et al. PLoS One 2014, 9 (11), page e110086, both mechanins have been shown to be corrected by 4-phenylbutyrate. These results suggest that sodium phenylbutyrate could be used in the treatment of dystonia.

Inclusion body myositis is a degenerative muscle disease characterized by progressive weakness and wasting of muscles of the arms and legs. There are two general types of IBM: sporadic and hereditary. As described in Nogalska et al. Neurobiol. Dis. 2014, 65, pages 93-101, sodium phenylbutyrate has been shown to reverse lysosomal dysfunction in an in vitro model of inclusion-body myositis, involving cultured human muscle fibers. Sodium phenylbutyrate was shown to improve lysosomal activity, decrease Aβ42 and its oligomers, decrease γ-secretase activity, and prevent muscle-fiber vacuolization. Accordingly, sodium phenylbutyrate could be used in the treatment of sporadic inclusion body myositis.

The commercially available formulations of immediate release sodium phenylbutyrate (e.g., BUPHENYL®) are unpalatable due to taste that is highly unpleasant. Noncompliance due to the poor taste can lead to insufficient dosing and suboptimal outcomes. The present invention addresses the need to improve patient compliance, by providing a palatable sodium phenylbutyrate formulation that is biologically active and bioequivalent to BUPHENYL®.

SUMMARY OF THE INVENTION

The present invention features palatable pharmaceutical compositions including sodium phenylbutyrate and methods for the treatment of inborn errors of metabolism (e.g., MSUD or UCD) with such compositions.

Accordingly, the invention features pharmaceutical compositions for oral administration containing sodium phenylbutyrate and a taste-mask coating, e.g., a taste-mask coating is insoluble at the neutral pH of the mouth and soluble at the acidic pH of the stomach, methods of manufacturing such compositions, and uses thereof. A non-limiting example of a taste-mask coating with these properties is a polymer formed from dimethylaminoethyl methacrylate, butyl methacrylate, and methyl methacrylate (e.g., a cationic polymer such as Eudragit EPO). In some embodiments, the dosage form of the composition may be a plurality of small particles each having a taste-mask coating or a tablet that includes a taste-mask coating. Given the high doses of sodium phenylbutyrate generally required for the treatment of inborne errors of metabolism such as UCD and MSUD, high drug loading formulations to minimize the amount of material a patient must ingest are desirable.

In some embodiments, the composition of the invention is a plurality of spray layered particles or beads for oral administration. In some embodiments, the spray layered particle has a seed core or a substrate onto which a drug layer is coated followed by a taste-mask coat layer. In addition to these coats the composition may include other coats (e.g., seal coats, barrier coats). In some embodiments, the composition includes a particle containing at least 15% total weight sodium phenyl butyrate. In some embodiments, the composition includes a particle containing greater than 50% sodium phenyl butyrate. In some embodiments, the composition includes a particle including a taste-mask coat that is at least 5% but not more than 50% of the total weight of the particle.

In an aspect, the invention features a taste-masked pharmaceutical composition (e.g., a taste-masked and immediate release composition) including sodium phenylbutyrate and a pharmaceutically acceptable carrier, wherein (i) less than 15% (e.g., less than 10%, less than 5%, less than 1%) of the sodium phenylbutyrate in the composition dissolves in a transfer dissolution test at neutral pH (e.g., pH 6-8, pH 6.5-7.5, pH of about 6, pH of about 7, pH of about 8, pH of about 6.8) over a period of 10 minutes; and (ii) at least 95% (e.g., at least 96%, at least 97%, at least 98%, at least 99%) of the sodium phenylbutyrate in the composition dissolves in a transfer dissolution test at an acidic pH (e.g., pH 1-5, pH 1-2, pH of about 1, pH of about 2, pH of about 3, pH of about 4, pH of about 5, pH of about 1.2) over a period of 60 minutes.

In some embodiments, the composition includes a taste-mask coating including a coating that is insoluble at a neutral pH (e.g., pH>5) and soluble at an acidic pH (e.g., pH<2) such as a polymer formed from dimethylaminoethyl methacrylate, butyl methacrylate, and methyl methacrylate (e.g., Eudragit E PO). In some embodiments, the composition includes 5-50% by total weight (e.g., 5-15%, 10-25%, 20-30%, 25-35%, 30-40%, 35-45%, or 40-50% by total weight or at least 5%, at least 10%, at least 15%, at least 20%, at least 25%, at least 30%, at least 35%, at least 40%, or at least 45% by total weight, or less than 10%, less than 15%, less than 20%, less than 25%, less than 30%, less than 35%, less than 40%, less than 45%, or less than 50% by total weight) of the taste-mask coating.

In some embodiments, the composition includes 15-60% by total weight (e.g., 20-30%, 25-35%, 30-40%, 35-45%, 40-50%, 45-55%, or 50-60% by total weight or at least 15%, at least 20%, at least 25%, at least 30%, at least 35%, at least 40%, at least 45%, at least 50%, at least 55%, or at least 60% by total weight, or less than 20%, less than 25%, less than 30%, less than 35%, less than 40%, less than 45%, less than 50%, less than 55%, or less than 60% by total weight) of sodium phenylbutyrate.

In some embodiments, the composition includes 3-10% by total weight (e.g., 3-5%, 4-6%, 5-7%, 6-8%, 7-9%, or 8-10% by total weight, or at least 3%, at least 4%, at least 5%, at least 6%, at least 7%, at least 8%, at least 9%, or at least 10% by total weight, or less than 3%, less than 4%, less than 5%, less than 6%, less than 7%, less than 8%, less than 9%, or less than 10% by total weight) of a binder (e.g., hydroxypropyl methylcellulose such as HPMC E 5, hydroxypropylcellulose, polyvinylalcohol, polyvinylpyrrolidone).

In some embodiments, the composition includes 0.1-7% by total weight (e.g., 0.2-1%, 0.5-3%, 2-5%, 3-7%) of a plasticizer (e.g., polyethylene glycol such as a polyethylene glycol having a molecular weight between 5,000 and 7,000 such as PEG6000, or triethylcitrate). In some embodiments, the composition does not include a plasticizer.

In some embodiments, the composition includes 4-15% by total weight (e.g., 4-6%, 5-7%, 6-8%, 7-9%, or 8-10% by total weight, or at least 4%, at least 5%, at least 6%, at least 7%, at least 8%, or at least 9% total weight, or less than 4%, less than 5%, less than 6%, less than 7%, less than 8%, less than 9%, or less than 10%) of a hydrated magnesium silicate (e.g., talc).

In some embodiments, the composition includes 1-5% by total weight (e.g., includes 3-4%, 3.5-4.5%, 4-5% by total weight, or at least 1%, at least 2%, at least 3%, or at least 4% by total weight, or less than 2%, less than 3%, less than 4%, or less than 5% by total weight) of a seal coat including a water soluble polymer such as a polyvinyl alcohol (e.g., Opadry such as Opadry Clear). In some embodiments, the composition does not include a seal coat.

In some embodiments of any of the foregoing compositions, the composition is formulated as taste-mask coated tablets (e.g., tablets produced using standard pharmaceutical excipients such as fillers, binders, glidants, lubricant; manufacturing processes such as blending, milling, dry granulation, wet granulation, compression; and coated with a taste-mask coating, e.g. a taste-mask coating including a polymer formed from dimethylaminoethyl methacrylate, butyl methacrylate, and methyl methacrylate such as Eudragit EPO), taste-mask coated mini-tablets (e.g., tablets with a diameter of less than 4 mm produced using standard pharmaceutical excipients such as fillers, binders, glidants, lubricant; manufacturing processes such as blending, milling, dry granulation, wet granulation, compression; and coated with a taste-mask coating, e.g. a taste-mask coating including a polymer formed from dimethylaminoethyl methacrylate, butyl methacrylate, and methyl methacrylate such as Eudragit EPO), or taste-mask coated beads produced by spray-layering, extrusion spheronization, rotor granulation, or melt congealing methods.

In another aspect, the invention features a pharmaceutical composition for oral administration of sodium phenylbutyrate including 15-60% by total weight (e.g., 20-30%, 25-35%, 30-40%, 35-45%, 40-50%, 45-55%, or 50-60% by total weight or at least 15%, at least 20%, at least 25%, at least 30%, at least 35%, at least 40%, at least 45%, at least 50%, at least 55%, or at least 60% by total weight, or less than 20%, less than 25%, less than 30%, less than 35%, less than 40%, less than 45%, less than 50%, less than 55%, or less than 60% by total weight) of the sodium phenylbutyrate in a drug layer and 5-50% by total weight (e.g., 5-15%, 10-25%, 20-30%, 25-35%, 30-40%, 35-45%, or 40-50% by total weight or at least 5%, at least 10%, at least 15%, at least 20%, at least 25%, at least 30%, at least 35%, at least 40%, or at least 45% by total weight, or less than 10%, less than 15%, less than 20%, less than 25%, less than 30%, less than 35%, less than 40%, less than 45%, or less than 50% by total weight) of a taste-mask coating including a coating that is insoluble at a neutral pH (e.g., pH>5) and soluble at an acidic pH (e.g., pH<2) such as a polymer formed from dimethylaminoethyl methacrylate, butyl methacrylate, and methyl methacrylate (e.g., Eudragit E PO).

In some embodiments, the drug layer further includes 3-10% by total weight (e.g., 3-5%, 4-6%, 5-7%, 6-8%, 7-9%, or 8-10% by total weight, or at least 3%, at least 4%, at least 5%, at least 6%, at least 7%, at least 8%, at least 9%, or at least 10% by total weight, or less than 3%, less than 4%, less than 5%, less than 6%, less than 7%, less than 8%, less than 9%, or less than 10% by total weight) of a binder (e.g., hydroxypropyl methylcellulose such as HPMC E 5, hydroxypropylcellulose, polyvinylalcohol, polyvinylpyrrolidone).

In some embodiments, the drug layer further includes 0.1-1% by total weight (e.g., 0.2-0.6 or about 0.5%) of a plasticizer (e.g., polyethylene glycol such as a polyethylene glycol having a molecular weight between 5,000 and 7,000 such as PEG6000, or triethylcitrate). In some embodiments, the drug layer does not include a plasticizer.

In some embodiments, the taste-mask coating further includes 1-9% by total weight (e.g., 3-5%, 4-6%, 5-7%, 6-8%, or 7-9% by total weight, or at least 3%, at least 4%, at least 5%, at least 6%, at least 7%, or at least 8% by total weight or less than 3%, less than 4%, less than 5%, less than 6%, less than 7%, less than 8%, or less than 9%) of a plasticizer (e.g., polyethylene glycol such as a polyethylene glycol having a molecular weight between 5,000 and 7,000 such as PEG6000, or triethylcitrate).

In some embodiments, the taste-mask coating further includes 4-15% by total weight (e.g., 4-6%, 5-7%, 6-8%, 7-9%, or 8-10% by total weight, or at least 4%, at least 5%, at least 6%, at least 7%, at least 8%, or at least 9% total weight, or less than 4%, less than 5%, less than 6%, less than 7%, less than 8%, less than 9%, or less than 10%) of a hydrated magnesium silicate (e.g., talc).

In some embodiments, the taste-mask coating includes 5-30% by total weight of a polymer formed from dimethylaminoethyl methacrylate, butyl methacrylate, and methyl methacrylate (e.g., Eudragit E PO). In some embodiments, a polymer formed from dimethylaminoethyl methacrylate, butyl methacrylate, and methyl methacrylate (e.g., Eudragit E PO) comprises 50-75% by weight of the taste-mask coating.

In some embodiments, the composition further includes 1-50% by total weight (e.g., 1-10%, 5-15%, 10-20%, 15-25%, 20-30%, 25-35%, 30-40%, 35-45%, or 40-50% by total weight, or at least 5%, at least 10%, at least 15%, at least 20%, at least 25%, at least 30%, at least 35%, at least 40%, at least 45%, at least 50% by total weight, or less than 5%, less than 10%, less than 15%, less than 20%, less than 25%, less than 30%, less than 35%, less than 40%, less than 45%, less than 50% by total weight) of a seed core (e.g., microcrystalline cellulose, sugar spheres, starch spheres, or other inert spherical pharmaceutically acceptable material).

In some embodiments, the composition further includes 1-5% by total weight (e.g., includes 3-4%, 3.5-4.5%, 4-5% by total weight, or at least 1%, at least 2%, at least 3%, or at least 4% by total weight, or less than 2%, less than 3%, less than 4%, or less than 5% by total weight) of a seal coat including a water soluble polymer such as a polyvinyl alcohol (e.g., Opadry such as Opadry Clear).

In some embodiments, the composition includes 5-50% (e.g., 5-35%. 15-35%, 15-50%) by total weight of the taste-mask coating.

In some embodiments, the composition includes 15-60% (e.g., 15-35%, 15-25%) by total weight of sodium phenylbutyrate.

In some embodiments, the pharmaceutical composition includes 44-46% by total weight cellulose pellets; 22-24% by total weight sodium phenylbutyrate; 5-7% by total weight HPMC E5; 3-4% by total weight of Opadry Clear; 4-6% by total weight of a PEG6000; 12-14% by total weight of a polymer formed from dimethylaminoethyl methacrylate, butyl methacrylate, and methyl methacrylate (e.g., Eudragit E PO); and 5-7% by total weight of talc.

In some embodiments the pharmaceutical composition includes about 45% by total weight cellulose pellets, about 23% by total weight sodium phenylbutyrate, about 6% by total weight HPMC E5, about 3% by total weight of Opadry Clear, about 5% by total weight of a PEG6000; about 13% by total weight of a polymer formed from dimethylaminoethyl methacrylate, butyl methacrylate, and methyl methacrylate (e.g., Eudragit E PO), and about 6% by total weight of talc.

In another aspect, the invention features a pharmaceutical composition including: a. 38-40% by total weight cellulose pellets; b. 8-20% by total weight sodium phenylbutyrate; c. 5-7% by total weight HPMC E5; d. 3-4% by total weight of Opadry Clear; e. 5-7% by total weight of PEG6000; f. 17-19% by total weight of a polymer formed from dimethylaminoethyl methacrylate, butyl methacrylate, and methyl methacrylate (e.g., Eudragit E PO); and g. 8-10% by total weight of talc.

In another aspect, the invention features a pharmaceutical composition of including: a. about 39% by total weight cellulose pellets; b. about 19% by total weight sodium phenylbutyrate; c. about 6% by total weight HPMC E5; d. about 3% by total weight of Opadry Clear; e. about 6% by total weight of PEG6000; f. about 18% by total weight of a polymer formed from dimethylaminoethyl methacrylate, butyl methacrylate, and methyl methacrylate (e.g., Eudragit E PO); and g. about 9% by total weight of talc.

In another aspect, the invention features a pharmaceutical composition including: a. 44-46% by total weight cellulose pellets; b. 22-24% by total weight sodium phenylbutyrate; c. 5-7% by total weight HPMC E5; d. 3-4% by total weight of Opadry Clear; e. 4-6% by total weight of PEG6000; f. 12-14% by total weight of a polymer formed from dimethylaminoethyl methacrylate, butyl methacrylate, and methyl methacrylate (e.g., Eudragit E PO); and g. 5-7% by total weight of talc.

In another aspect, the invention features a pharmaceutical composition of including: a. about 45% by total weight cellulose pellets; b. about 23% by total weight sodium phenylbutyrate; c. about 6% by total weight HPMC E5; d. about 3% by total weight of Opadry Clear; e. about 5% by total weight of PEG6000; f. about 13% by total weight of a polymer formed from dimethylaminoethyl methacrylate, butyl methacrylate, and methyl methacrylate (e.g., Eudragit E PO); and g. about 6% by total weight of talc.

In some embodiments, the pharmaceutical composition includes 44-46% by total weight cellulose pellets; 22-24% by total weight sodium phenylbutyrate; 5-7% by total weight HPMC E5; 3-4% by total weight of Opadry Clear; 2-4% by total weight of a PEG6000; 14-16% by total weight of a polymer formed from dimethylaminoethyl methacrylate, butyl methacrylate, and methyl methacrylate (e.g., Eudragit E PO); and 7-9% by total weight of talc.

In some embodiments the pharmaceutical composition includes about 45% by total weight cellulose pellets, about 23% by total weight sodium phenylbutyrate, about 6% by total weight HPMC E5, about 3% by total weight of Opadry Clear, about 3% by total weight of a PEG6000; about 15% by total weight of a polymer formed from dimethylaminoethyl methacrylate, butyl methacrylate, and methyl methacrylate (e.g., Eudragit E PO), and about 8% by total weight of talc.

In another aspect, the invention features a pharmaceutical composition including: a. 32-34% by total weight cellulose pellets; b. 15-17% by total weight sodium phenylbutyrate; c. 3-5% by total weight HPMC E5; d. 2-3% by total weight of Opadry Clear; e. 3-4% by total weight of PEG6000; f. 27-29% by total weight of a polymer formed from dimethylaminoethyl methacrylate, butyl methacrylate, and methyl methacrylate (e.g., Eudragit E PO); and g. 13-15% by total weight of talc.

In another aspect, the invention features a pharmaceutical composition of including: a. about 33% by total weight cellulose pellets; b. about 16% by total weight sodium phenylbutyrate; c. about 4% by total weight HPMC E5; d. about 2% by total weight of Opadry Clear; e. about 3% by total weight of PEG6000; f. about 28% by total weight of a polymer formed from dimethylaminoethyl methacrylate, butyl methacrylate, and methyl methacrylate (e.g., Eudragit E PO); and g. about 14% by total weight of talc.

In another aspect, the invention features a pharmaceutical composition including: a. 15-17% by total weight cellulose pellets; b. 45-50% by total weight sodium phenylbutyrate; c. 4-6% by total weight HPMC E5; e. 2-3% by total weight of PEG6000; f. 20-22% by total weight of a polymer formed from dimethylaminoethyl methacrylate, butyl methacrylate, and methyl methacrylate (e.g., Eudragit E PO); and g. 7-9% by total weight of talc.

In another aspect, the invention features a pharmaceutical composition of including: a. about 16% by total weight cellulose pellets; b. about 48% by total weight sodium phenylbutyrate; c. about 5% by total weight HPMC E5; e. about 3% by total weight of PEG6000; f. about 21% by total weight of a polymer formed from dimethylaminoethyl methacrylate, butyl methacrylate, and methyl methacrylate (e.g., Eudragit E PO); and g. about 8% by total weight of talc.

In another aspect, the invention features a pharmaceutical composition including: a. 6-8% by total weight cellulose pellets; b. 65-70% by total weight sodium phenylbutyrate; c. 6-8% by total weight HPMC E5; e. 1-3% by total weight of PEG6000; f. 12-14% by total weight of a polymer formed from dimethylaminoethyl methacrylate, butyl methacrylate, and methyl methacrylate (e.g., Eudragit E PO); and g. 4-6% by total weight of talc.

In another aspect, the invention features a pharmaceutical composition of including: a. about 7% by total weight cellulose pellets; b. about 67% by total weight sodium phenylbutyrate; c. about 7% by total weight HPMC E5; e. about 2% by total weight of PEG6000; f. about 13% by total weight of a polymer formed from dimethylaminoethyl methacrylate, butyl methacrylate, and methyl methacrylate (e.g., Eudragit E PO); and g. about 5% by total weight of talc.

In another aspect, the invention features a pharmaceutical composition including: a. 4-6% by total weight cellulose pellets; b. 45-50% by total weight sodium phenylbutyrate; c. 4-6% by total weight HPMC E5; e. 3-4% by total weight of PEG6000; f. 28-30% by total weight of a polymer formed from dimethylaminoethyl methacrylate, butyl methacrylate, and methyl methacrylate (e.g., Eudragit E PO); and g. 11-13% by total weight of talc.

In another aspect, the invention features a pharmaceutical composition of including: a. about 5% by total weight cellulose pellets; b. about 47% by total weight sodium phenylbutyrate; c. about 5% by total weight HPMC E5; e. about 3% by total weight of PEG6000; f. about 29% by total weight of a polymer formed from dimethylaminoethyl methacrylate, butyl methacrylate, and methyl methacrylate (e.g., Eudragit E PO); and g. about 12% by total weight of talc.

In another aspect, the invention features a pharmaceutical composition including: a. 6-7% by total weight cellulose pellets; b. 60-65% by total weight sodium phenylbutyrate; c. 8-10% by total weight HPMC E5; e. 2-3% by total weight of PEG6000; f. 15-17% by total weight of a polymer formed from dimethylaminoethyl methacrylate, butyl methacrylate, and methyl methacrylate (e.g., Eudragit E PO); and g. 5-7% by total weight of talc.

In another aspect, the invention features a pharmaceutical composition of including: a. about 7% by total weight cellulose pellets; b. about 61% by total weight sodium phenylbutyrate; c. about 9% by total weight HPMC E5; e. about 3% by total weight of PEG6000; f. about 16% by total weight of a polymer formed from dimethylaminoethyl methacrylate, butyl methacrylate, and methyl methacrylate (e.g., Eudragit E PO); and g. about 6% by total weight of talc.

In another aspect, the invention features a pharmaceutical composition including: a. 4-6% by total weight cellulose pellets; b. 42-47% by total weight sodium phenylbutyrate; c. 6-8% by total weight HPMC E5; e. 3-4% by total weight of PEG6000; f. 28-30% by total weight of a polymer formed from dimethylaminoethyl methacrylate, butyl methacrylate, and methyl methacrylate (e.g., Eudragit E PO); and g. 11-13% by total weight of talc.

In another aspect, the invention features a pharmaceutical composition of including: a. about 5% by total weight cellulose pellets; b. about 45% by total weight sodium phenylbutyrate; c. about 7% by total weight HPMC E5; e. about 4% by total weight of PEG6000; f. about 29% by total weight of a polymer formed from dimethylaminoethyl methacrylate, butyl methacrylate, and methyl methacrylate (e.g., Eudragit E PO); and g. about 12% by total weight of talc.

In some embodiments of any of the foregoing compositions, the composition is formulated as spray-layered beads. In some embodiments of any of the foregoing compositions, the composition is formulated as taste-masked beads produced by extrusion/spheronization, rotor granulation, or melt congeal methods.

In some embodiments, any of the foregoing compositions may be tested in an in vitro dissolution transfer test in which the composition is subjected to a neutral pH for a predetermined period of time and then transferred to an acidic pH for a predetermined period of time. The release of sodium phenylbutyrate is monitored at each pH to determine the rate of dissolution of the sodium phenylbutyrate from the composition.

In some embodiments of any of the foregoing compositions, less than 15% (e.g., less than 10%, less than 5%, less than 1%) of the sodium phenylbutyrate in the composition is dissolved in a transfer dissolution test at neutral pH (e.g., pH 6-8, pH 6.5-7.5, pH of about 6.8) over a period of 10 minutes.

In some embodiments of any of the foregoing compositions, at least 95% of sodium phenylbutyrate in the composition is dissolved once transferred to an acidic pH (e.g., pH 1-5, pH 1-2, pH about 1.2) in a transfer dissolution test over a period of 60 minutes.

In some embodiments of any of the foregoing compositions, at least 95% of sodium phenylbutyrate in the composition is dissolved in a transfer dissolution test at an acidic pH (e.g., pH 1-5, pH 1-2, pH about 1.2) over a period of 30 minutes.

In some embodiments of any of the foregoing compositions, upon administration to a subject, the composition has equivalent distribution in plasma compared to BUPHENYL®. In some embodiments of any of the foregoing compositions, the composition is bioequivalent to BUPHENYL®.

In some embodiments of any of the foregoing compositions, upon administration to a subject, the composition has greater sodium phenylbutyrate levels in the plasma at 30 minutes compared to an modified release formulation (e.g., RAVICTI®) of sodium phenylbutyrate.

In some embodiments of any of the foregoing compositions, the composition scores favorably in a taste test in comparison to BUPHENYL®.

The invention also features methods of manufacturing pharmaceutical compositions for oral administration containing sodium phenylbutyrate and a taste-mask coating, e.g., a taste-mask coating is insoluble at the neutral pH of the mouth and soluble at the acidic pH of the stomach.

In some embodiments of any of the foregoing compositions, the taste-mask coated beads may be administered in a dosing vehicle with a viscosity of approximately 50-1750 centipoise (cP), e.g., to aid suspension and dosing of the beads. One type of suspending agent that can be used is modified corn starch or a combination of modified food starch and maltodextrin (e.g., THICK-IT®). For example, any of the foregoing compositions may be administered with approximately 1-4 teaspoons (tsp) of THICK-IT® added per 120 mL of water to achieve this viscosity range. An appropriate quantity of taste-masked beads can be added to the THICK-IT® water mixture and agitated to suspend the beads just prior to administration.

Other suspending agents may also be used as a dosing vehicle. Exemplary suspending agents include agar, alginic acid, sodium carboxymethyl cellulose, carrageenan, dextrin, gelatin, guar gum, hydroxyethyl cellulose, hydroxypropyl cellulose, Hypromellose, methyl cellulose, polyethylene glycol, povidone, tragacanth, xanthan gum, or other suspending agents known in the art.

Additionally, the dosing vehicle may further contain flavoring agents, fragrances, dyes (colors), sweeteners, anti-caking agents, glidants (flow enhancers), and lubricants.

In some embodiments of any of the foregoing compositions, the taste-mask coated beads may have a volume-based particle size distribution in which 90% of the beads in the composition are smaller than about 500 µM, i.e. $DV_{90}$ approximately 500 µm, (e.g., smaller than 500 µM, smaller than 400 µM, smaller than 300 µM).

Accordingly, in another aspect, the disclosure provides a method of manufacturing a pharmaceutical composition including sodium phenyl butyrate by providing a core including cellulose pellets, applying a first layer including sodium phenylbutyrate, hydroxypropyl methylcellulose (e.g., HPMC E 5), and polyethylene glycol (e.g., a PEG having a molecular weight between 5,000 and 7,000 such as PEG6000), applying a second layer including a polyvinyl alcohol (e.g., an Opadry such as Opadry Clear), and applying a third layer including a derivative of methyacrylic acid (e.g., a polymer formed from the copolymerization of dimethylaminoethyl methacrylate, butyl methacrylate, and methyl methacrylate such as Eudragit E PO), a polyethylene glycol (e.g., a PEG having a molecular weight between 5,000 and 7,000 such as PEG6000), and hydrated magnesium silicate (e.g., talc), thereby manufacturing a pharmaceutical composition including sodium phenyl butyrate.

In some embodiments of the method, the final composition includes 1-50% by total weight (e.g., 0-10%, 5-15%, 10-20%, 15-25%, 20-30%, 25-35%, 30-40%, 35-45%, or 40-50% by total weight, or at least 5%, at least 10%, at least 15%, at least 20%, at least 25%, at least 30%, at least 35%, at least 40%, or at least 45% by total weight, or less than 5%, less than 10%, less than 15%, less than 20%, less than 25%, less than 30%, less than 35%, less than 40%, less than 45%, less than 50% by total weight) of cellulose pellets.

In some embodiments of the method, the final composition includes a first layer including 15-60% by total weight (e.g., 20-30%, 25-35%, 30-40%, 35-45%, 40-50%, 45-55%, or 50-60% by total weight, or at least 15%, at least 20%, at least 25%, at least 30%, at least 35%, at least 40%, at least 45%, at least 50%, at least 55% by total weight or less than 20%, less than 25%, less than 30%, less than 35%, less than 40%, less than 45%, less than 50%, less than 55%, or less than 60% by total weight) of sodium phenylbutyrate, 3-10% by total weight (e.g., 3-5%, 4-6%, 5-7%, 6-8%, 7-9, or 8-10% by total weight, or at least 3%, at least 4%, at least 5%, at least 6%, at least 7%, at least 8%, or at least 9% by total weight, or less than 3%, less than 4%, less than 5%, less than 6%, less than 7%, less than 8%, less than 9%, or less than 10% by total weight) of hydroxypropyl methylcellulose, and less than 1% by total weight (e.g., 0.001-0.1%, 0.01%-0.2%, 0.1-0.3%, 0.2-0.5%, 0.4-0.6%, 0.5-0.7%, 0.6-0.8%, 0.7-0.9%, or 0.8-1.0% by total weight, or at least 0.001%, at least 0.01%, at least 0.1%, at least 0.2%, at least 0.3%, at least 0.4%, at least 0.5%, at least 0.6%, at least 0.7%, at least 0.8%, or at least 0.9% by total weight or less than 0.001%, less than 0.01%, less than 0.1%, less than 0.2%, less than 0.3%, less than 0.4%, less than 0.5%, less than 0.6%, less than 0.7%, less than 0.8%, less than 0.9%, or less than 1% by total weight) of polyethylene glycol.

In some embodiments of the method, the final composition includes a second layer including 3-5% by total weight (e.g., 3-4%, 3.5-4.5%, or 4-5% by total weight, or at least 3%, at least 3.5%, at least 4%, or at least 4.5%, or less than 3.5%, less than 4%, less than 4.5%, or less than 5% by total weight) of polyvinyl alcohol.

In some embodiments of the method, the final composition includes a third layer including 10-15% (e.g., 10-12%, 11-13%, 12-15%, or 14-15% by total weight, or at least 10%, at least 11%, at least 12%, at least 13%, or at least 14% by total weight, or less than 10%, less than 11%, less than 12%, less than 13%, less than 14%, or less than 15%) total weight of a polymer formed from dimethylaminoethyl methacrylate, butyl methacrylate, and methyl methacrylate (e.g., Eudragit E PO), 3-10% by total weight (e.g., 3-5%, 4-6%, 5-7%, 6-8%, 7-9, or 8-10% by total weight, or at least 3%, at least 4%, at least 5%, at least 6%, at least 7%, at least 8%, or at least 9% by total weight, or less than 3%, less than 4%, less than 5%, less than 6%, less than 7%, less than 8%, less than 9%, or less than 10%) of polyethylene glycol, and 4-15% (e.g., 4-6%, 5-7%, 6-8%, 7-9%, or 8-10% by total weight, or at least 4%, at least 5%, at least 6%, at least 7%, at least 8%, or at least 9% by total weight, or less than 4%, less than 5%, less than 6%, less than 7%, less than 8%, less than 9%, or less than 10% by total weight) of hydrated magnesium silicate.

In some embodiments of any of the foregoing methods, the first layer is applied in water.

In some embodiments of any of the foregoing methods, the second layer is applied in water.

In some embodiments of any of the foregoing methods, the third layer is applied in organic solvent such as a solution of acetone and isopropyl alcohol.

In another aspect, the invention features a pharmaceutical composition prepared by any of the foregoing methods.

In another aspect, the invention features a method of treating an inborn error of metabolism (e.g., maple syrup urine disease or urea cycle disorder) in a subject including administering an effective amount of any of the foregoing pharmaceutical compositions.

In another aspect, the invention features a method of treating a neurodegenerative disorder (e.g., Parkinson's disease) in a subject including administering an effective amount of any of the foregoing pharmaceutical compositions.

In another aspect, the invention features a method of treating spinal muscular atrophy in a subject including administering an effective amount of any of the foregoing pharmaceutical compositions.

In another aspect, the invention features a method of treating dystonia in a subject including administering an effective amount of any of the foregoing pharmaceutical compositions.

In another aspect, the invention features a method of treating inclusion-body myositis in a subject including administering an effective amount of any of the foregoing pharmaceutical compositions.

In some embodiments of any of the foregoing methods, the subject is a human.

In some embodiments of any of the foregoing methods, the pharmaceutical composition is administered in a dosing vehicle with a viscosity of approximately 50-1750 centipoise (cP), e.g., to aid suspension and dosing of the beads. One type of suspending agent that can be used is modified corn starch or a combination of modified food starch and maltodextrin (e.g., THICK-IT®). For example, any of the foregoing compositions may be administered with approximately 1-4 teaspoons (tsp) of THICK-IT® added per 120 mL of water to achieve this viscosity range. An appropriate quantity of taste-masked beads can be added to the THICK-IT®/water mixture and agitated to suspend the beads just prior to administration.

Other suspending agents may also be used as a dosing vehicle. Exemplary suspending agents include agar, alginic acid, sodium carboxymethyl cellulose, carrageenan, dextrin, gelatin, guar gum, hydroxyethyl cellulose, hydroxypropyl cellulose, Hypromellose, methyl cellulose, polyethylene glycol, povidone, tragacanth, xanthan gum, or other suspending agents known in the art. Additionally, the dosing vehicle may further contain flavoring agents, fragrances, dyes (colors), sweeteners, anti-caking agents, glidants (flow enhancers), and lubricants.

Definitions

About: As used herein, the term "about" when used in the context of the amount of a component of a composition means +/−10% of the recited value.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Animal: As used herein, the term "animal" refers to any member of the animal kingdom. In some, particularly therapeutic, embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately", as applied to one or more values of interest refers to a value that is similar to a stated reference value. In certain embodiments, the term "approximately" or refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binder: As used herein, the term "binder," refers to an excipient that holds the ingredients in a formulation together or holds ingredients onto a substrate (e.g., the seed core). Binders ensure that tablets and granules can be formed with required mechanical strength, and give volume to low active dose tablets. Examples of binders include, but are not limited to, hydroxypropylmethylcellulose such as HPMC E 5, saccharides and their derivatives, protein such as gelatin, sugar alcohols such as xylitol, sorbitol or maltitol, or synthetic polymers such as polyvinylpyrrolidone or polyethyleneglycol.

Bioequivalent: As used herein, the term "bioequivalent," refers to the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. As understood by one of skill in the art, different types of evidence may be used to establish bioequivalence for pharmaceutically equivalent drug products, including in vivo (e.g., Cmax and/or AUC data) or in vitro (e.g., rate of dissolution) testing, or both. The selection of the method used to demonstrate bioequivalence depends upon the purpose of the study, the analytical methods available, and the nature of the drug product. In some embodiments, bioequivalence may be established using any method described herein such as determining the plasma levels of sodium phenylbutyrate of two different formulations at different time points in healthy subjects.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention may be considered biologically active if even a portion of the polynucleotide is biologically active or mimics an activity considered biologically relevant.

By Total Weight: As used herein, the phrase "by total weight" refers to the amount of an ingredient in the composition as a percentage of the total weight of the total composition including all ingredients.

Delivery: As used herein, "delivery" refers to the act or manner of delivering a compound, substance, entity, moiety, cargo or payload.

Dosing Vehicle: As used herein, "dosing vehicle" refers to pharmaceutically acceptable excipients (e.g., thickeners or suspension agents), or combinations thereof, that aid in the administration of a pharmaceutical formulation.

Equivalent Distribution: As used herein, "equivalent distribution," refers to distribution, e.g., as measured in plasma, of phenylbutyrate from one formulation that is substantially similar (e.g., within 10%, within 5%, within 2%, within 1%) of the distribution of another formulation.

Modified Release Formulation: As used herein, "modified release formulation," refers to a formulation of phenylbutyrate, or a pharmaceutically acceptable salt thereof, in which the phenyl butyrate is released such that there is a significant difference in the rate (e.g., the rate is significantly slower) and extent of absorption of the active pharmaceutical ingredient compared to BUPHENYL®. An approved modified release formulation of phenylbutyrate is Glycerol phenylbutyrate which is sold under the trade name RAVICTI® and approved for use in the treatment of UCD.

Formulation: As used herein, a "formulation" includes at least sodium phenyl butyrate and a delivery agent.

Greater Distribution: As used herein, the term "greater distribution" refers to distribution, e.g., as measured in plasma, of phenylbutyrate from one formulation that is greater than (e.g., at least 5% greater, at least 10% greater, at least 20% greater, at least 50% greater) the distribution of another formulation.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Lubricant: As used herein, the term "lubricant," refers to a compound that prevents the ingredients in a formulation from clumping together, prevents clumping of the completed composition (e.g., of the spray-layered beads), or prevents sticking of ingredients to surfaces (e.g., equipment used in the manufacture and/or processing of the composition). Examples of lubricants include, but are not limited to, talc, silica, and fats such as vegetable stearin, magnesium stearate, or stearic acid.

Organic solvent: As used herein, "organic solvent," refers to a carbon-based substance that dissolves a solute (a chemically different liquid, solid, or gas), resulting in a solution, wherein the substance is not water.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient" or "pharmaceutically acceptable carrier," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, thickeners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltodextrin, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (e.g., modified food or corn starch), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is altered by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's *The Science and Practice of Pharmacy*, 21St Edition, A. R. Gennaro (Lippincott, Williams & Wilkins, Baltimore, Md., 2006); *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Plasticizer: As used herein, the term "plasticizer," refers to an additive that increases the plasticity or fluidity of a formulation. Plasticizers are used to control the film formation process of coatings based on physically drying film forming materials. Proper film formation is essential in order to meet demands on specific coating properties such as dry film appearance, substrate adhesion, elasticity, in combination with high level of hardness at the same time. Examples of plasticizers useful in the formulations and methods of the invention include, but are not limited to, polyethylene glycols such as PEG6000 or triethylcitrate.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Scores favorably in a Taste Test: As used herein, the term "scores favorably in a taste test" refers to a formulation which scores higher in a taste test (e.g., any taste test known in the art) than another formulation. Different taste tests are known in the art, e.g., formulations may be tested for palatability using any appropriate taste test known in the art such by a flavor profile test. The flavor profile method uses trained evaluators, such as a panel of 1, 2, 3, 4, 5, 6, 7, 8, 9, 10 or more experts, to identify, characterize, and quantify the perceived sensory attributes of a formulation. Attributes identified by the panel are basic tastes (sweet, sour, salty, bitter, umami), aromatics (flavoring aromatics and aromatic "off-notes"), feeling factors (cooling, numbing, bite/burn, etc.), and amplitude (perception of balance and fullness). The perceived strength or intensity of each of these attributes will be measured an assigned an appropriate value: 0 for none, 1 for slight, 2 for moderate, and 3 for strong. Chemical reference standards are used to establish the intensity scale for on-going panelist calibration. Additionally, all sensations remaining in the aftertaste are measured at selected intervals over 1, 5, 10, 15 or more minutes.

Seal coat: As used herein, the term "seal coat," refers to a layer of compound(s) that prevents direct contact of two layers of the composition. In some embodiments, the seal coat protects the ingredients in a formulation from deterioration by moisture in the air. In some embodiments, the seal coat protects the ingredients from deterioration due to contact with ingredients in another layer. Examples of compounds which may be used in a seal coat include, but are not limited to, Opadrys such as Opadry Clear, polyvinyl alcohols, hydroxypropylcellulose, hydroxypropylmethylcellulose, or polyvinylpyrrolidone.

Seed core: As used herein, the term "seed core," refers to a surface on which ingredients of a formulation may be applied. Examples of seed cores useful in the invention, include, but are not limited to, microcrystalline cellulose pellets, sugar spheres, starch spheres, or other inert spherical pharmaceutically acceptable materials. In some embodiments, the seed core is about 100 µm to 1.5 mm in diameter.

Significant or Significantly: As used herein, the terms "significant" or "significantly" are used synonymously with the term "substantially."

Single unit dose: As used herein, a "single unit dose" is a dose of any therapeutic administered in one dose/at one time/single route/single point of contact, i.e., single administration event.

Spray-layered Bead: As used herein, the term "spray-layered bead" refers to spherical multiparticulates (e.g., 100- to 1,500-µm in size) with one or more coating layers applied by fluidized-bed coating technology. Sucrose or microcrystalline substrates such as microcrystalline cellulose are typically utilized with the coat layers containing one or more drug substances. Extruded beads or lipid multiparticulates may also be spray layered coated. In some embodiments, the multiparticulates are comprise compressed drug substances which are then coated with one or more layers (e.g., a taste-mask coat).

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Taste-mask coat: As used herein, the term "taste-mask coat," refers to a layer of compound(s) that prevents release of the sodium phenylbutyrate in the oral cavity and allow its release in the stomach to mask the unpleasant taste of sodium phenylbutyrate. In some embodiments, a taste-mask coating refers to a layer of compound(s) that results in a formulation that scores favorably in a taste test. Examples of compounds useful in taste-mask coats for the formulations and methods of the invention include, but are not limited to, a polymer formed from dimethylaminoethyl methacrylate, butyl methacrylate, and methyl methacrylate (e.g., Eudragit E PO) and other coatings that dissolve at the pH of the stomach, but are insoluble at the pH of the mouth.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, "therapeutically effective amount" refers to the amount of a compound that, when administered to a mammal for treating a state, disorder or condition (e.g., an inborn error of metabolism, such as MSUD), is sufficient to effect such treatment. The "therapeutically effective amount" will vary depending on the compound, the disease and its severity, and the age, weight, physical condition and responsiveness of the mammal to be treated. As used herein the term "therapeutically effective amount" refers to an amount of a compound sufficient to prevent, inhibit, reduce, or eliminate one or more causes, symptoms, or complications of elevated plasma levels of branched chain amino acids and/or branched chain alpha-ketoacids (e.g., levels in an individual with an inborn error of metabolism, such as MSUD) compared to the plasma levels in a subject that does not have an inborn error of metabolism (e.g., a healthy subject and/or a subject with normal levels of branched chain amino acids and/or branched chain alpha-ketoacid). In certain embodiments, a desired therapeutic effect is the attainment of target plasma levels (e.g., 200-500 μmol/L leucine, 100-200 μmol/L isoleucine, and 100-300 μmol/L valine) of at least one branched chain amino acid and/or branched chain alpha-ketoacid for the individual. In certain embodiments, a desired therapeutic effect is the attainment of normal plasma levels (e.g., 65-220 μmol/L leucine, 26-100 μmol/L isoleucine, and 90-300 μmol/L valine) of at least one branched chain amino acid. In specific embodiments, the treatment is considered therapeutically effective when there is a particular extent of reduction in the plasma level of one or more branched chain amino acids and/or branched chain alpha-ketoacids. In certain cases, the treatment is considered therapeutically effective when there is a reduction of at least 5%, 7.5%, 10%, 12.5%, 15%, 17.5%, 20%, 22.5%, 25%, 27.5%, 30%, 32.5%, 35%, 37.5%, 40%, 42.5%, 45%, 47.5%, or 50% of the plasma level of one or more branched chain amino acids and/or branched chain alpha-ketoacids or when there is a reduction of at least about 5%, 7.5%, 10%, 12.5%, 15%, 17.5%, 20%, 22.5%, 25%, 27.5%, 30%, 32.5%, 35%, 37.5%, 40%, 42.5%, 45%, 47.5%, or 50% of the plasma level of one or more branched chain amino acids and/or branched chain alpha-ketoacids. The skilled artisan recognizes that plasma levels may be measured by standard methods in the art, for example using a plasma amino acid test or urine amino acid test by chromatography and/or mass spectrometry.

Total daily dose: As used herein, a "total daily dose" is an amount given or prescribed in 24 hr period. It may be administered as a single unit dose.

Transfer dissolution test. As used herein, the term "transfer dissolution test" refers to an in vitro test of the release of sodium phenylbutyrate from a formulation. The dissolution of sodium phenylbutyrate may be determined using any method in the art. For example, the dissolution of sodium phenylbutyrate in a formulation of sodium phenylbutyrate, may be determined following the dissolution assay protocol described below.

A pH 6.8 potassium phosphate buffer solution (USP) was prepared, and 700 mL of the solution was added to a Distek 2500 USP II (paddle) dissolution apparatus. The bath was heated to 37.5 C and 1 gm of sodium phenylbutyrate multiparticulates was added while being agitated at 100 RPM. Samples of the dissolution media (1.5 mL) were collected at t=5, 10 and 15 minutes. After the 15 minute sample was taken 100 mL of 1 N hydrochloric acid solution was added to the dissolution vessel, and the volume was adjusted to 900 mL by adding a pH 1.2 0.1 N HCl solution (USP). The dissolution test continued for another 65 minutes, and 1.5 mL samples were collected at t=20, 30, 40, 50, 60, 70 and 80 minutes. After the 80 minute sample was taken the agitation was increased to 300 RPM for an additional 15 minutes, and a final 1.5 mL sample was taken at t=95 minutes. A Shimadzu Prominence-I LC-2030C 3D HPLC system was used to measure the drug release in all samples.

Treating: As used herein, "treating" or "treatment" of a state, disorder or condition includes: (1) preventing or delaying the appearance of clinical symptoms of the state, disorder or condition developing in a mammal that may be afflicted with or predisposed to the state, disorder or condition, but does not yet experience or display clinical or subclinical symptoms of the state, disorder or condition; (2) inhibiting the state, disorder or condition, i.e., arresting or reducing the development of the disease or at least one clinical or subclinical symptom thereof; or (3) relieving the disease, i.e., causing regression of the state, disorder or condition or at least one of its clinical or subclinical symptoms.

DETAILED DESCRIPTION OF THE INVENTION

Figure 1A:
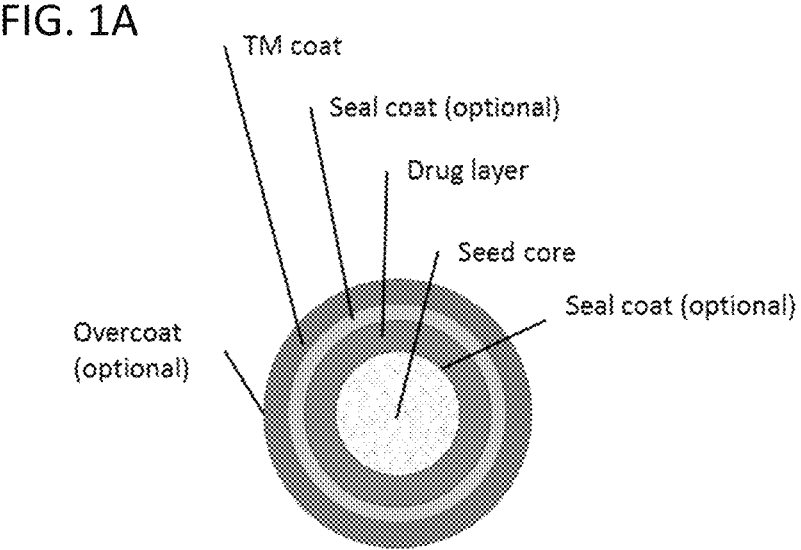
FIG. 1A is a schematic of a taste-masked particle with a seed core.

The invention described herein features taste-masked formulations of sodium phenylbutyrate and methods of using the formulations in the treatment of inborn errors of metabolism such as MSUD and UCD, neurodegenerative disorders such as Parkinson's disease, spinal muscular atrophy, inclusion-body myositis, or dystonia. The formulations of sodium phenylbutyrate of the invention address known issues with treatment noncompliance, due to poor taste, and consequent insufficient dosing with commercially available formulations of sodium phenylbutyrate such as BUPHENYL®. The formulations of the invention are taste-masked, pH sensitive formulations with rapid distribution of the active ingredient, sodium phenylbutyrate, e.g., as measured in the plasma of a subject. In some embodiments, the formulations include a high drug load.

Methods of Producing Taste-Masked Compositions

Taste-masked materials may be prepared by first identifying a suitable seed core such as cellulose pellets, followed by preparation of a solution including sodium phenylbutyrate. The sodium phenylbutyrate containing solution may be prepared by combing in a solution of HPMC E 5 and PEG 6000 in purified water with a separate solution of sodium phenylbutyrate in purified water. The sodium phenylbutyrate-containing layer is than applied to the seed core by spraying, followed by drying and storage of the coated pellets.

A seal coat solution is prepared by mixing Opadry Clear in purified water, followed by application onto the dried drug-containing pellets by spraying. The pellets with the seal coat are then dried and stored.

A taste mask coating solution is then prepared in a 2:3 parts acetone:IPA solution to which a polymer formed from dimethylaminoethyl methacrylate, butyl methacrylate, and methyl methacrylate (e.g., Eudragit E PO) is added. The solution containing a polymer formed from dimethylaminoethyl methacrylate, butyl methacrylate, and methyl methacrylate (e.g., Eudragit E PO) is then combined with another solution containing homogenized talc and PEG 6000.

The taste-mask coating solution is then applied to the seal coated pellets by spraying. Subsequent drying of the pellets results in the finished powder taste-masked formulation. In some embodiments, the final composition (e.g., spray-layered beads) is blended with a lubricant such as silica, e.g., to prevent agglomeration of the composition.

Prior to administration, the taste-masked formulation may be combined with a dosing vehicle that contains various pharmaceutically acceptable excipients such as viscosity modifiers, suspending or dispering agents, flavoring agents, fragrances, dyes (colors), sweeteners, anti-caking agents, glidants (flow enhancers), and lubricants.

The dosing vehicle may be mixed with the taste-masked formulation and added to water and stirred, or the dosing vehicle may be added first to the water and mixed before addition of the taste-masked formulation.

Other palatable liquids may be used instead of water provided that the pH of the liquid is ≥6.

Methods of Treatment

The present invention features pharmaceutical compositions in an orally tolerable formula that contains a therapeutically effective amount of sodium phenylbutyrate. In some embodiments the pharmaceutical composition is a granular formulation that is dispersed in a pharmaceutically acceptable carrier, for example the composition can be mixed into water and ingested by a patient (e.g., over the course of 5 to 10 minutes). Suitable formulations for use in the present invention are found in Remington's Pharmaceutical Sciences, Mack Publishing Company, Philadelphia, Pa. $22^{nd}$ ed., 2010. Except insofar as any conventional carrier is incompatible with the active ingredient, its use in the pharmaceutical compositions is contemplated. Moreover, for animal (e.g., human) administration, it will be understood that preparations should meet sterility, pyrogenicity, general safety and purity standards as required by FDA Office of Biological Standards.

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

Maple Syrup Urine Disease

For the treatment of MSUD the actual dosage amount can be determined, in part, by measuring the levels of branched chain amino acids (BCAAs) in the plasma and adjusting dosage to decrease the plasma level of at least one BCAA to within a range that is accepted to be non-toxic and supports optimal growth and development (Table 1).

TABLE 1

| Target Ranges for BCAAs | | |
| --- | --- | --- |
| Branched Chain Amino Acid | Target Levels (μmol/L) | Normal Reference Range (μmol/L) |
| Leucine | 200-500 | 65-220 |
| Isoleucine | 100-200 | 26-100 |
| Valine | 100-300 | 90-300 |

Urea Cycle Disorders

Sodium phenyl butyrate is approved as an adjunctive therapy in the chronic management of subjects with UCD. Sodium phenylbutyrate is indicated for all patients with neonatal-onset deficiency and subjects with late-onset disease who have a history of hyperammonemic encephalopathy. Sodium phenylbutyrate is generally administered in combination with dietary protein restriction and often with essential amino acids supplementation.

The usual total daily dose of BUPHENYL® Tablets and Powder for patients with urea cycle disorders is 450-600 mg/kg/day in patients weighing less than 20 kg, or 9.9-13.0 g/m²/day in larger patients. The tablets and powder are to be taken in equally divided amounts with each meal or feeding (i.e., three to six times per day). In some embodiments, the pharmaceutical compositions of the present invention are bioequivalent to BUPHENYL® and, therefore, equivalent dosage of sodium phenylbutyrate would be likely be useful for the treatment of UCD.

Spinal Muscular Atrophy

Sodium phenyl butyrate has been investigated as a treatment for infants with spinal muscular atrophy. The target dose of BUPHENYL® powder for patients with spinal muscular atrophy is 450-600 mg/kg/day, divided into four doses. In some embodiments, the pharmaceutical compositions of the present invention are bioequivalent to BUPHENYL® and, therefore, equivalent dosage of sodium phenylbutyrate would be likely be useful for the treatment of spinal muscular atrophy.

Parkinson's Disease

For the treatment of Parkinson's disease the actual dosage amount can be determined, in part, by measuring the levels of biomarkers (e.g., the expression level of the gene DJ-1 as described in Zhou W. et al. J. Biol. Chem. 2011, 286 (17), pages 14941-14951) in the blood and adjusting dosage accordingly (e.g., to increase the expression level of DJ-1 without resulting in side effects).

Inclusion-Body Myositis

For the treatment of inclusion-body myositis, the actual dosage amount can be determined by measuring the levels of biomarkers, e.g., by measuring the lysosomal activity, amount of Aβ42 and its oligomers, γ-secretase activity, and/or muscle-fiber vacuolization as described in Nogalska et al.

Dystonia

For the treatment of dystonia, the actual dosage amount can be determined by measuring the levels of biomarkers, e.g., by measuring ER stress and/or the cyclic adenosine-3', 5'-monophosphate (cAMP) response to the adenylate cyclase agonist forskolin as described in Cho et al.

Dosages

The dosage of any composition described herein or identified using the methods described herein depends on several factors, including: the administration method, the disease (e.g., MSUD, UCD, Parkinson's disease, spinal muscular atrophy, inclusion-body myositis, or dystonia) to be treated, the severity of the disease, and the age, weight, and health of the subject to be treated.

With respect to the treatment methods of the invention, it is not intended that the administration of a composition to a subject be limited to a particular dosage, or frequency of dosing. The composition may be administered to the subject in a single dose or in multiple doses. For example, a composition described herein may be administered at least once a day (e.g., twice a day, three times a day, four times a day, or more). It is to be understood that, for any particular subject, specific dosage regimes should be adjusted over time according to the individual need and the professional judgment of the person administering or supervising the administration of the composition. For example, the dosage of a composition can be increased if the lower dose does not provide sufficient activity in the treatment of a disease or condition described herein (e.g., MSUD, UCD, Parkinson's disease, spinal muscular atrophy, inclusion-body myositis, or dystonia). Conversely, the dosage of the composition can be decreased if the disease (e.g., MSUD, UCD, Parkinson's disease, spinal muscular atrophy, inclusion-body myositis, or dystonia) is reduced.

While the attending physician ultimately will decide the appropriate amount and dosage regimen, a therapeutically effective amount of a composition described herein, may be, for example, in the range of approximately 450-600 mg/kg/day of sodium phenylbutyrate (e.g., a composition including 50% by weight sodium phenylbutyrate would require a dose of 900-1200 mg/kg/day to provide 450-600 mg/kg/day of sodium phenylbutyrate) for urea cycle disorder patients weighing less than 20 kg, or 9.9-13.0 g/m$^2$/day in larger patients. In some embodiments the total daily dosage is to be taken in equally divided amounts with each meal or feeding (i.e., three to six times per day).

In some embodiments a therapeutically effective amount of a composition described herein, may be, for example, in the range of approximately 450-600 mg/kg/day of sodium phenylbutyrate (e.g., a composition including 50% by weight sodium phenylbutyrate would require a dose of 900-1200 mg/kg/day to provide 450-600 mg/kg/day of sodium phenylbutyrate) in MSUD patients weighing less than 20 kg, or 9.9-13.0 g/m$^2$/day in larger patients. In some embodiments the total daily dosage is to be taken in equally divided amounts with each meal or feeding (i.e., three to twelve times per day).

Solid Dosage Forms for Oral Use

Figure 1B:
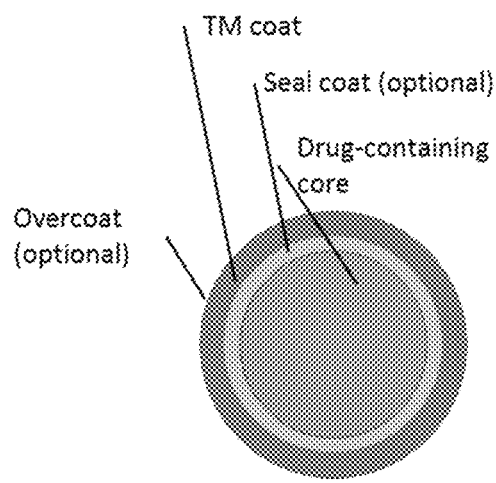
FIG. 1B is a schematic of a taste-masked particle with a drug containing core.
Figure 1C:
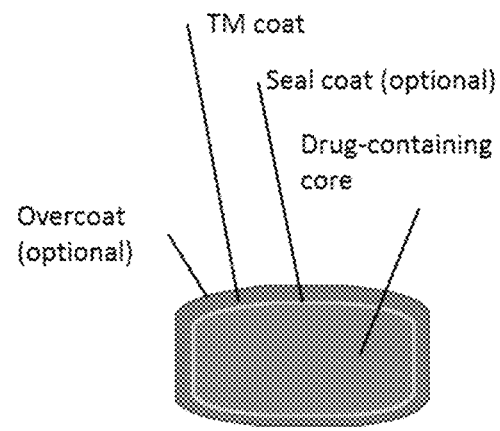
FIG. 1C is a schematic of a taste-masked tablet.

Formulations for oral use include particles containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). Some examples of solid dosage forms are shown in FIG. 1. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, and buffering agents. In some embodiments, excipients (e.g., flavoring agents) are packaged with the composition. In some embodiments, excipients (e.g., flavorings) are packaged separately from the composition (e.g., are combined with the composition prior to administration).

The solid compositions of the invention may include a coating adapted to protect the composition from unwanted chemical changes, (e.g., chemical degradation prior to the release of the active substances). The coating may be applied on the solid dosage form in a similar manner as that described in *Encyclopedia of Pharmaceutical Technology*, supra.

Powders and granulates may be prepared using the ingredients mentioned above in a conventional manner using, e.g., a mixer, a fluid bed apparatus, melt congeal apparatus, rotor granulator, extrusion/spheronizer, or spray drying equipment.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

EXAMPLES

Example 1. Preparation of Taste-Masked Formulations of Sodium Phenylbutyrate

Taste-masked materials may be prepared using the following methodology.

Drug Layering Solution

A solution of HPMC E 5 and PEG 6000 in purified water is made. A separate solution of sodium phenylbutyrate in purified water is also prepared. The two solutions are then combined to create the final drug layering solution of HPMC E 5, PEG 6000, and sodium phenylbutyrate in purified water.

Drug Layer Coating

Cellulose pellets are preheated to 35+/−2° C. in a GPCG-1 fluid bed with a 6" Wurster insert, and the drug layering solution is sprayed. Inlet air temperature is adjusted to maintain product temperature at 35-45 C during coating. After spraying, the coated pellets are dried for a minimum of 5 minutes at 40° C. The product is passed through 40#-70#screen, and stored in a polyethylene bag until the next solution is prepared.

Seal Coat Solution

A seal coat solution is prepared by mixing Opadry Clear in purified water for 30 minutes. The solution is passed through a 40#screen while being continuously stirred.

Seal Coating

The drug layered pellets are preheated to 35+/−2° C. in the GPCG-1 fluid bed with a 6" Wurster insert, and the seal coat solution is sprayed. Inlet air temperature is adjusted to maintain product temperature at 35-45° C. during coating. After spraying, the coated pellets are dried for a minimum of 5 minutes at 40° C. The product is passed through screen, and stored in a polyethylene bag until the next solution is prepared.

Taste-Mask Solution

A taste mask coating is prepared. A 2:3 parts acetone:IPA solution is mixed, and half is used to create a solution of Eudragit E PO. In a separate beaker the other half of solution is used to homogenize talc and PEG 6000. Both solutions are then combined before being filtered through a 40#screen.

Taste-Mask Coating

The seal coated pellets are preheated to 27+/−2° C. in the GPCG-1 fluid bed, and the taste mask coating is sprayed using bottom spray. Inlet air temperature is adjusted to maintain product temperature at 25-28° C. during coating. After spraying, the pellets are dried for a minimum of 10 minutes at 40° C., and stored in a polyethylene bag. A formulation with a 24 wt % taste-mask coat and 22 wt % drug load is presented in Table 2.

TABLE 2

Taste-mask coated formulation (24 wt % taste-mask coat, 22 wt % drug load)

| Layer | Ingredient | mg/g |
|---|---|---|
| Seed core | Microcrystalline cellulose pellets | 443.6 |
| Drug layer | Sodium phenylbutyrate | 221.8 |
|  | HPMC E 5 | 55.5 |
|  | PEG 6000 | 5.5 |
|  | (H2O) | — |
| Seal coat | Opadry Clear | 31.1 |
|  | (H2O) | — |
| Taste-mask coat | Eudragit E PO | 151.5 |
|  | PEG 6000 | 15.5 |
|  | Talc | 75.8 |
|  | (acetone) | — |
|  | (isopropyl alcohol) | — |

In Vitro Dissolution Testing

Figure 2:
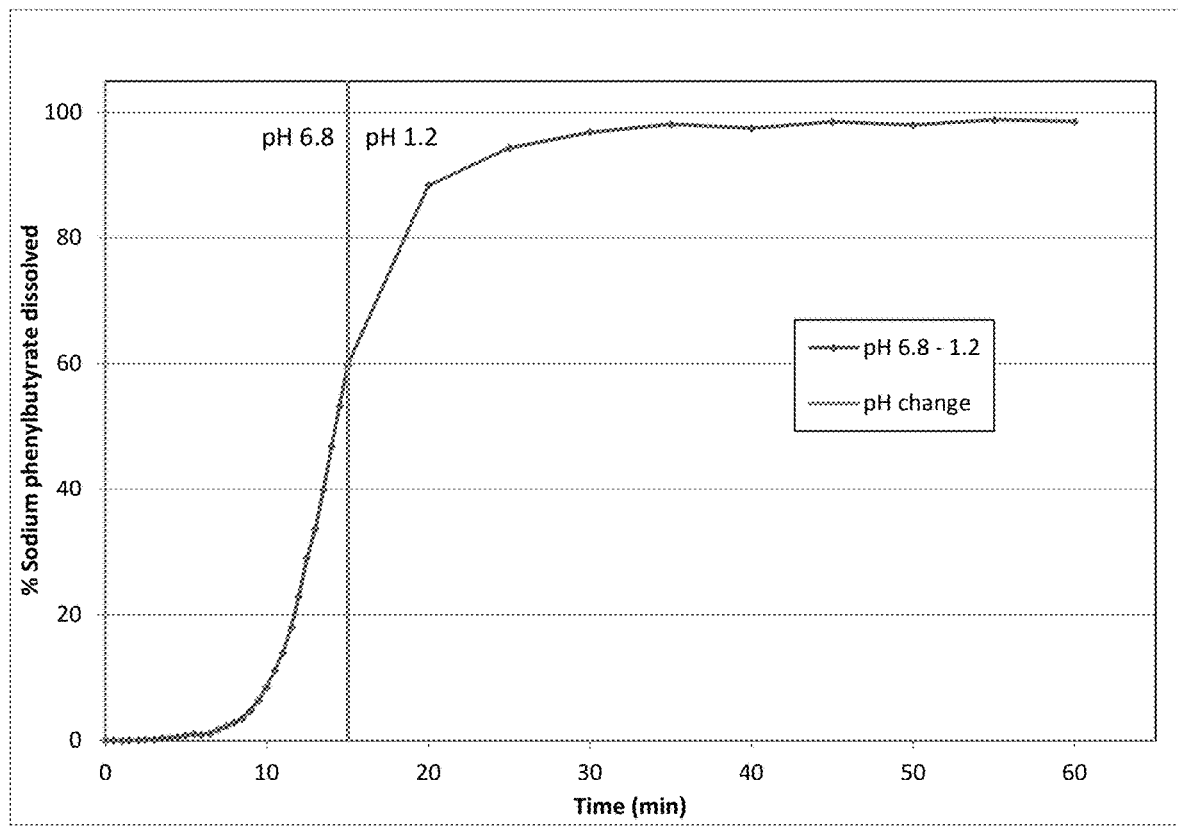
FIG. 2 is a graph illustrating drug release in a transfer dissolution test over time.

A pH 6.8 potassium phosphate buffer solution (USP) was prepared, and 700 mL of the solution was added to a Distek 2500 USP II (paddle) dissolution apparatus. The bath was heated to 37.5 C and 1 gm of sodium phenylbutyrate multiparticulates was added while being agitated at 100 RPM. Samples of the dissolution media (1.5 mL) were collected and drug release was measured with a Shimadzu Prominence-I LC-2030C 3D HPLC system. After the 15 minute sample was taken, 100 mL of 1 N hydrochloric acid solution was added to the dissolution vessel, and the volume was adjusted to 900 mL by adding a pH 1.2 0.1 N HCl solution (USP). The dissolution test continued for another 65 minutes, and data is presented in FIG. 2.

Example 2. Preparation of a Taste-Masked Formulation of Sodium Phenylbutyrate

Figure 3:
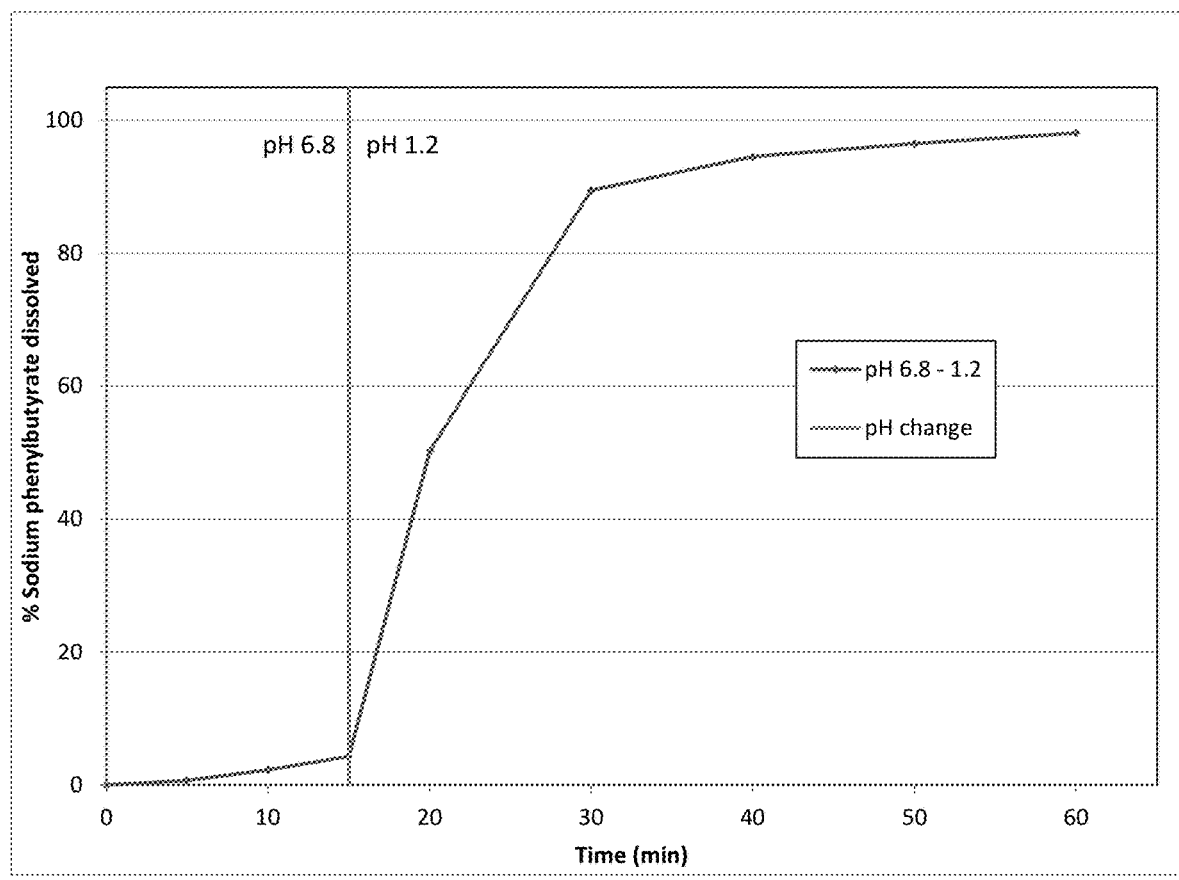
FIG. 3 is a graph illustrating drug release in a transfer dissolution test over time.

Taste-masked materials were prepared using the methodology described in Example 1 to achieve a formulation with a 44 wt % taste-mask coat and 16 wt % drug load. This formulation was dissolution tested as described in Example 1. The details of the formulation are presented in Table 3, and dissolution data is presented in FIG. 3.

TABLE 3

Taste-mask coated formulation (44 wt % taste-mask coat, 16 wt % drug load)

| Layer | Ingredient | mg/g |
|---|---|---|
| Seed core | Microcrystalline cellulose pellets | 325.3 |
| Drug layer | Sodium phenylbutyrate | 162.7 |
|  | HPMC E 5 | 40.7 |
|  | PEG 6000 | 4.1 |
|  | (H2O) | — |
| Seal coat | Opadry Clear | 22.8 |
|  | (H2O) | — |
| Taste-mask coat | Eudragit E PO | 277.8 |
|  | PEG 6000 | 27.7 |
|  | Talc | 138.9 |
|  | (acetone) | — |
|  | (isopropyl alcohol) | — |

Example 3. Preparation of a Taste-Masked Formulation of Sodium Phenylbutyrate

Figure 4:
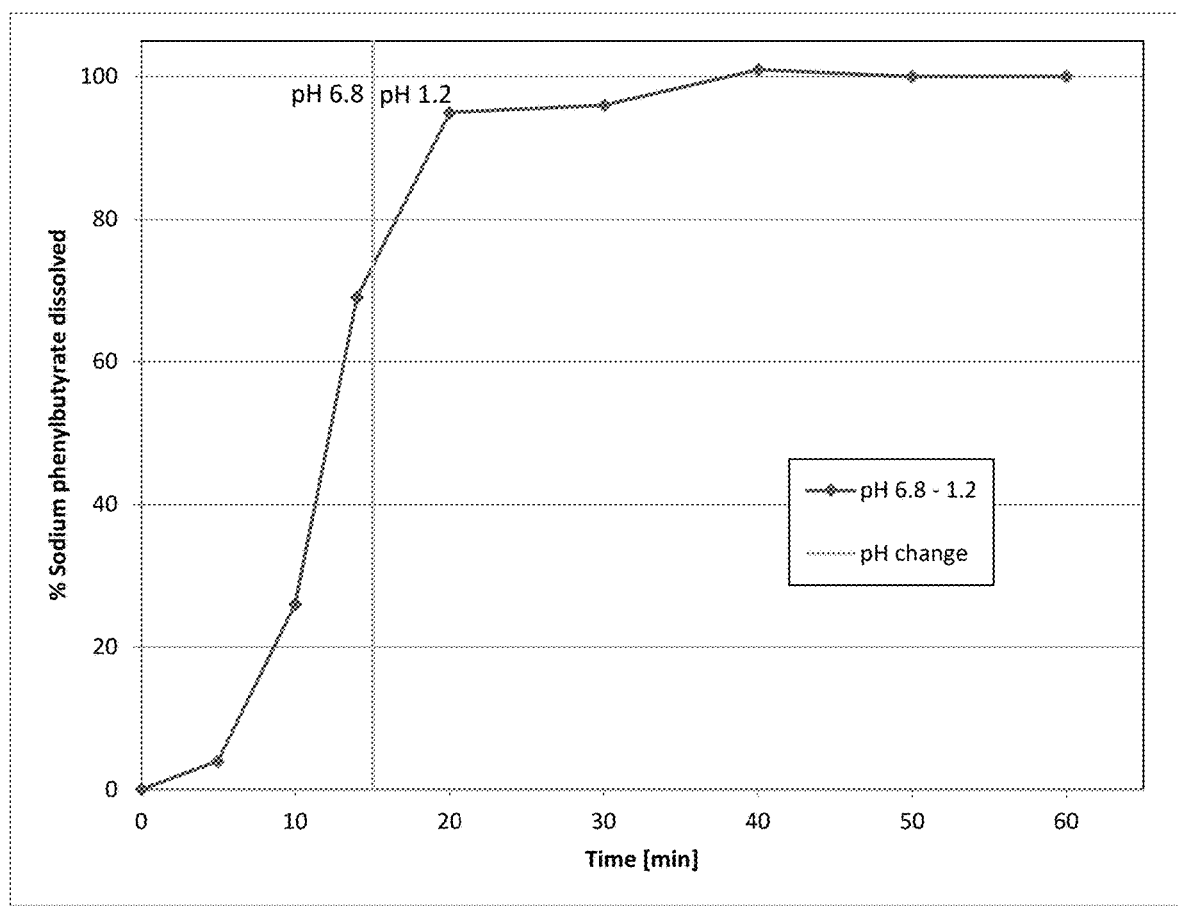
FIG. 4 is a graph illustrating drug release in a transfer dissolution test over time.

Taste-masked materials were prepared using the methodology described in Example 1, without the seal coat solution or coating steps, to achieve a formulation with a 31 wt % taste-mask coat and 47 wt % drug load. This formulation was dissolution tested as described in Example 1. The details of the formulation are presented in Table 4, and dissolution data is presented in FIG. 4.

TABLE 4

Taste-mask coated formulation (31 wt % taste-mask coat, 47 wt % drug load)

| Layer | Ingredient | mg/g |
|---|---|---|
| Seed core | Microcrystalline cellulose pellets | 161.4 |
| Drug layer | Sodium phenylbutyrate | 473.8 |
|  | HPMC E 5 | 47.4 |
|  | PEG 6000 | 7.1 |
|  | (H2O) | — |
| Taste-mask coat | Eudragit E PO | 206.9 |
|  | PEG 6000 | 20.6 |
|  | Talc | 82.8 |
|  | (acetone) | — |
|  | (isopropyl alcohol) | — |

Example 4. Preparation of a Taste-Masked Formulation of Sodium Phenylbutyrate

Figure 5:
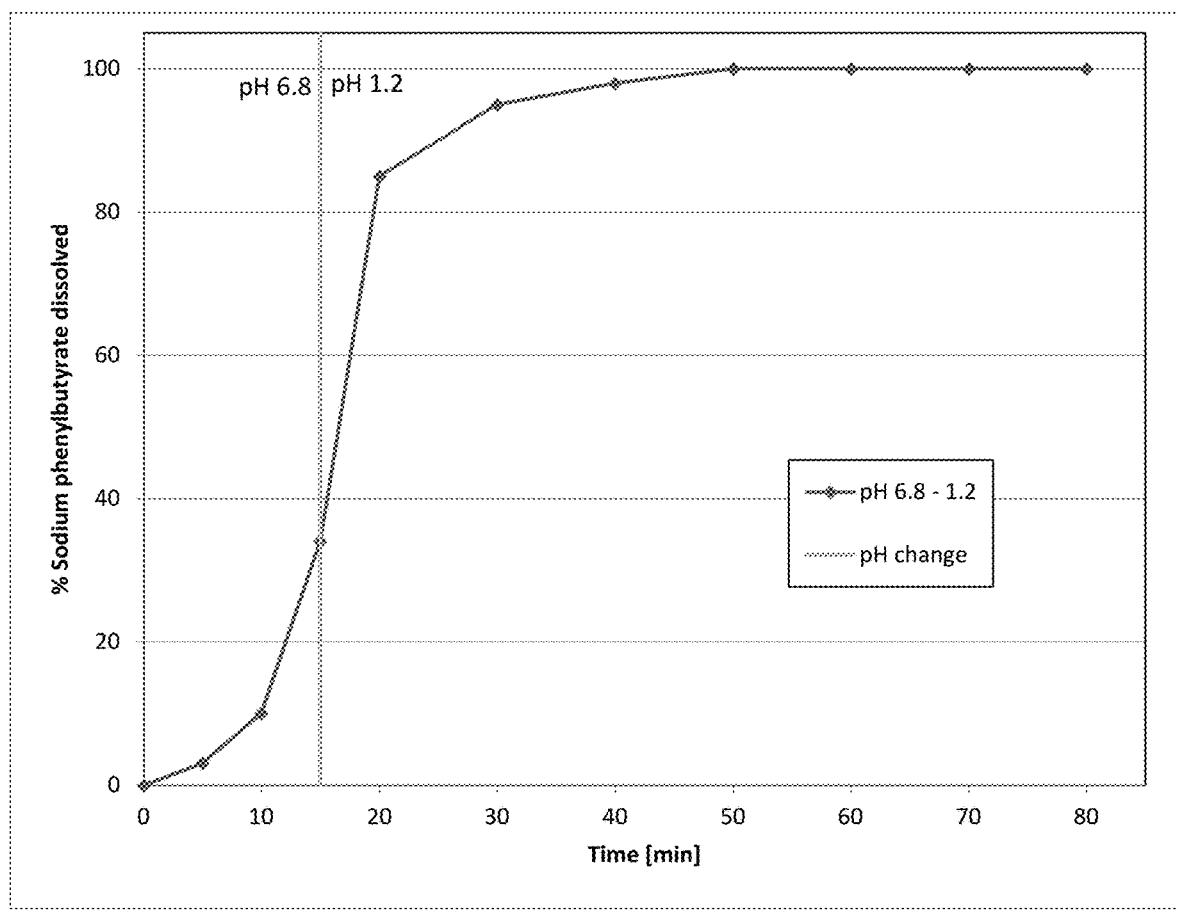
FIG. 5 is a graph illustrating drug release in a transfer dissolution test over time.

Taste-masked materials were prepared using the methodology described in Example 1, without the seal coat solution or coating steps, to achieve a formulation with an 18 wt % taste-mask coat and 67 wt % drug load. This formulation was dissolution tested as described in Example 1. The details of the formulation are presented in Table 5, and dissolution data is presented in FIG. 5.

TABLE 5

Taste-mask coated formulation (18 wt % taste-mask coat, 67 wt % drug load)

| Layer | Ingredient | mg/g |
|---|---|---|
| Seed core | Microcrystalline cellulose pellets | 73.2 |
| Drug layer | Sodium phenylbutyrate | 669.5 |
|  | HPMC E 5 | 67.0 |
|  | PEG 6000 | 6.7 |
|  | (H2O) | — |
| Taste-mask coat | Eudragit E PO | 122.5 |
|  | PEG 6000 | 12.2 |
|  | Talc | 49.0 |
|  | (acetone) | — |
|  | (isopropyl alcohol) | — |

Example 5. Preparation of a Taste-Masked Formulation of Sodium Phenylbutyrate

Figure 6:
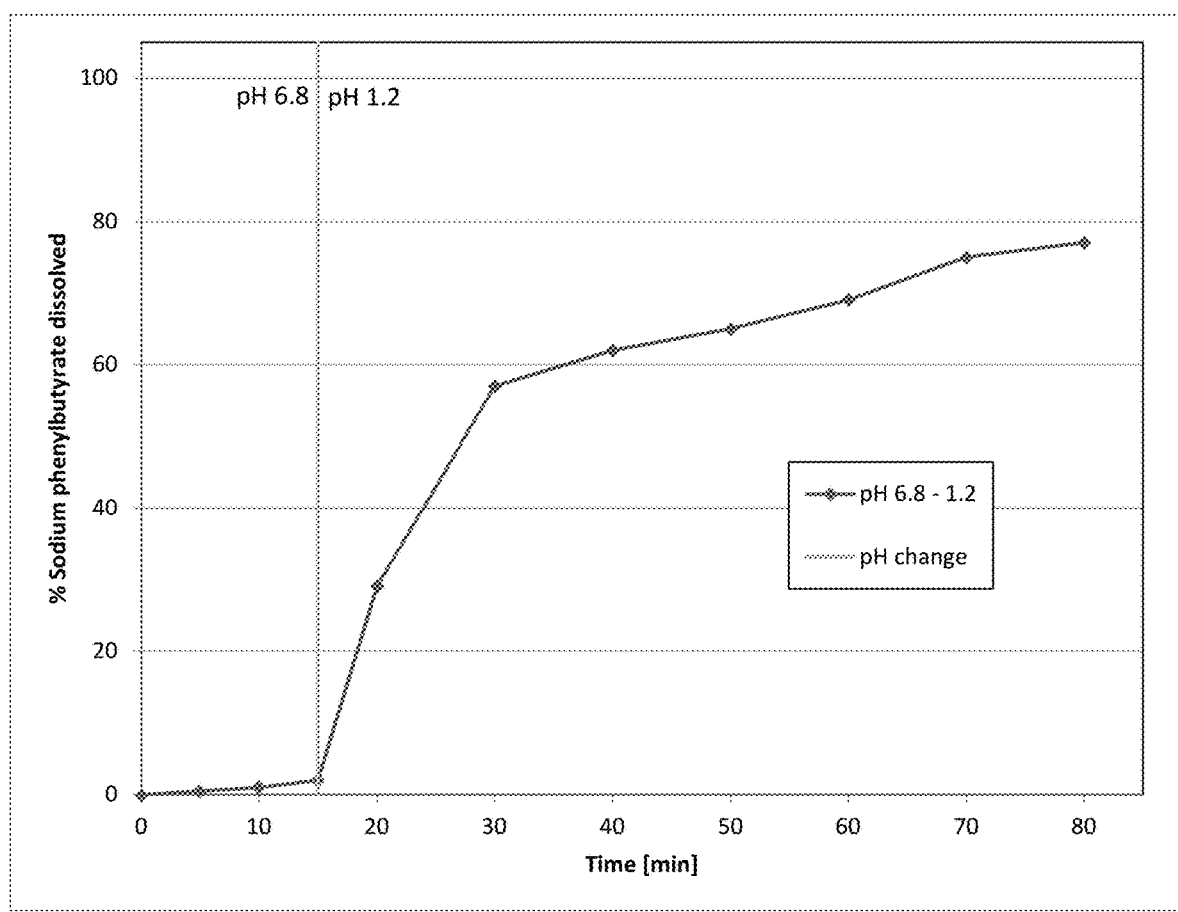
FIG. 6 is a graph illustrating drug release in a transfer dissolution test over time.

Taste-masked materials were prepared using the methodology described in Example 1, without the seal coat solution or coating steps, to achieve a formulation with a 43 wt % taste-mask coat and 47 wt % drug load. This formulation was dissolution tested as described in Example 1. The details of the formulation are presented in Table 6, and dissolution data is presented in FIG. 6.

TABLE 6

Taste-mask coated formulation (43 wt % taste-mask coat, 47 wt % drug load)

| Layer | Ingredient | mg/g |
|---|---|---|
| Seed core | Microcrystalline cellulose pellets | 51.2 |
| Drug layer | Sodium phenylbutyrate | 468.7 |
|  | HPMC E 5 | 46.9 |
|  | PEG 6000 | 4.7 |
|  | (H2O) | — |
| Taste-mask coat | Eudragit E PO | 285.7 |
|  | PEG 6000 | 28.5 |
|  | Talc | 114.3 |
|  | (acetone) | — |
|  | (isopropyl alcohol) | — |

Example 6. Preparation of a Taste-Masked Formulation of Sodium Phenylbutyrate

Figure 7:
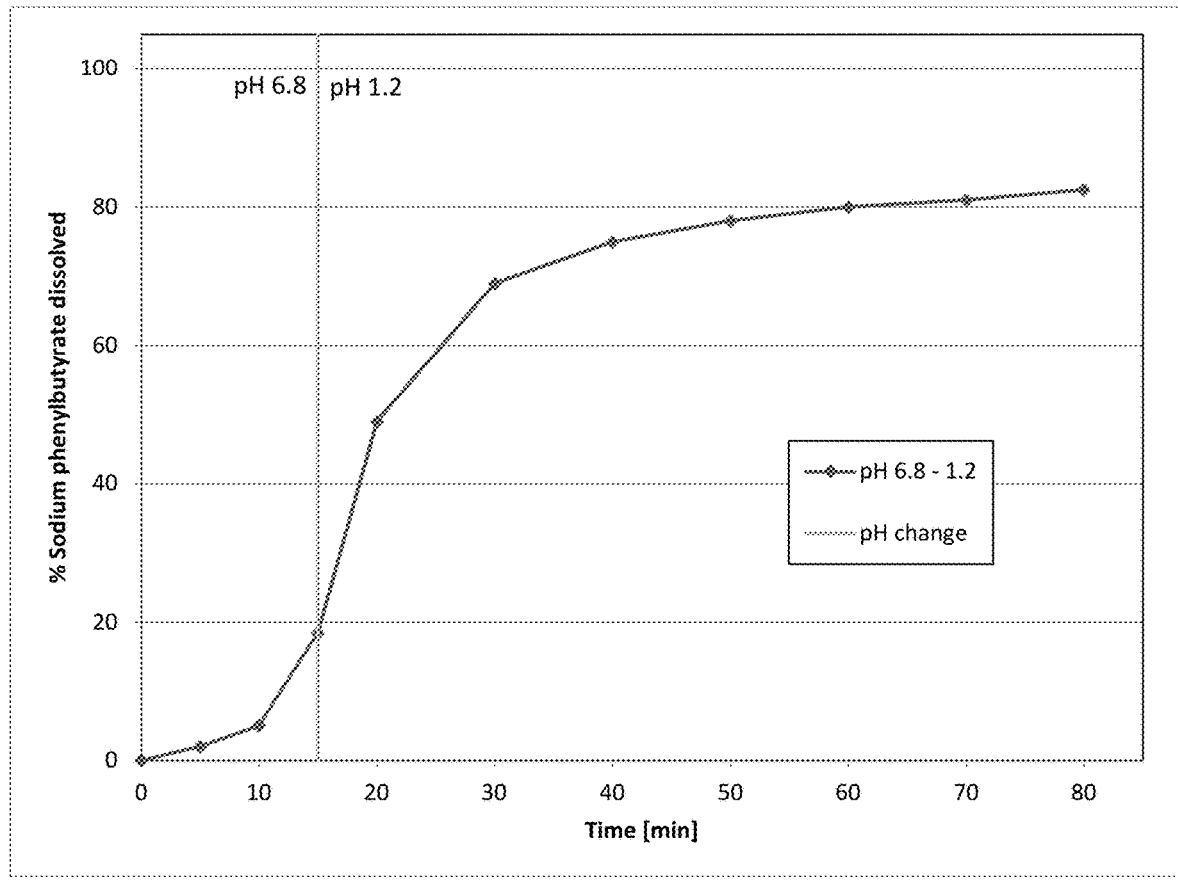
FIG. 7 is a graph illustrating drug release in a transfer dissolution test over time.

Taste-masked materials were prepared using the methodology described in Example 1, substituting a HPMC E 5 and PEG 6000 seal coat solution with the Opadry seal coat solution. The change to Example 1 was used to achieve a formulation with a 23 wt % taste-mask coat and 61 wt % drug load. This formulation was dissolution tested as described in Example 1. The details of the formulation are presented in Table 7, and dissolution data is presented in FIG. 7.

TABLE 7

| | Taste-mask coated formulation (23 wt % taste-mask coat, 61 wt % drug load) | |
|---|---|---|
| Layer | Ingredient | mg/g |
| Seed core | Microcrystalline cellulose pellets | 66.3 |
| Drug layer | Sodium phenylbutyrate | 606.6 |
| | HPMC E 5 | 60.7 |
| | PEG 6000 | 6.0 |
| | (H2O) | — |
| Seal coat | HPMC E 5 | 26.4 |
| | PEG 6000 | 3.2 |
| | (H2O) | — |
| Taste-mask coat | Eudragit E PO | 153.9 |
| | PEG 6000 | 15.4 |
| | Talc | 61.5 |
| | (acetone) | — |
| | (isopropyl alcohol) | — |

Example 7. Preparation of a Taste-Masked Formulation of Sodium Phenylbutyrate

Figure 8:
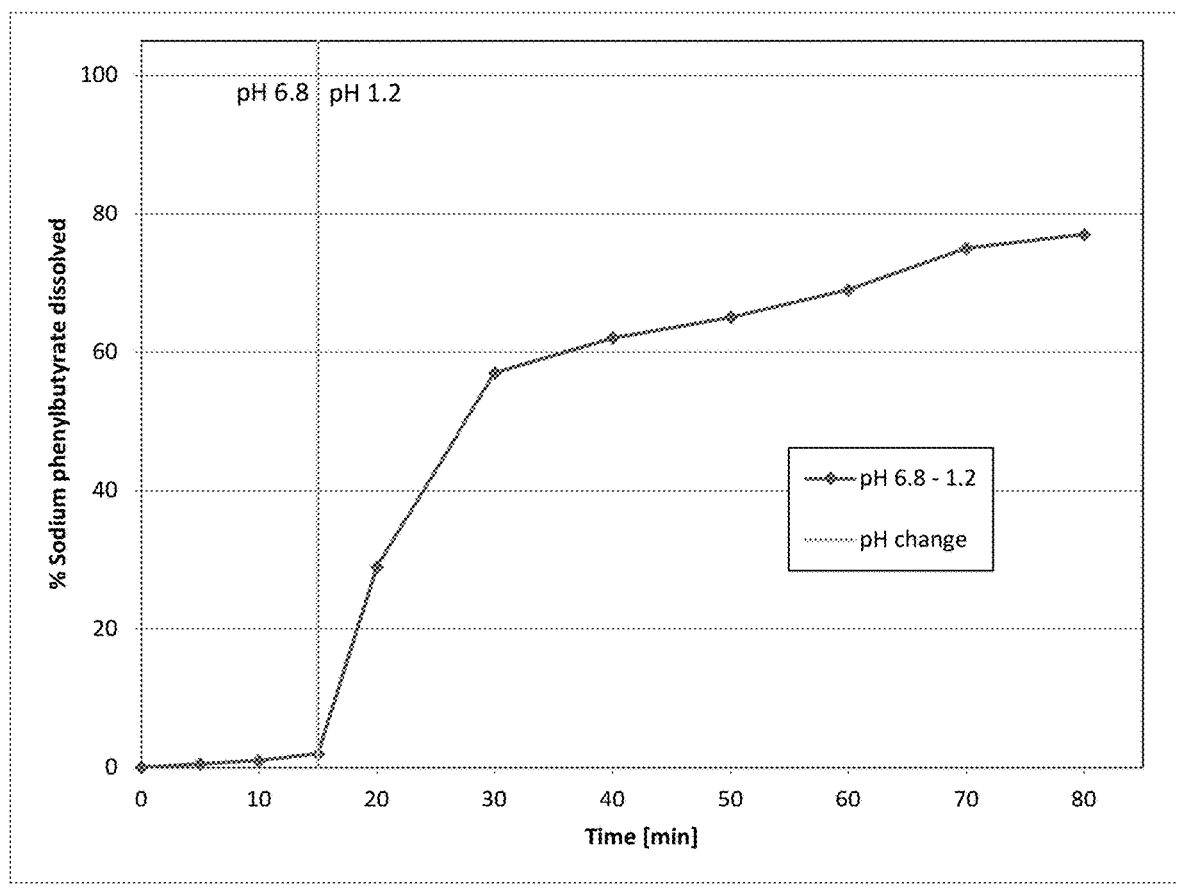
FIG. 8 is a graph illustrating drug release in a transfer dissolution test over time.

Taste-masked materials were prepared using the methodology described in Example 1, substituting a HPMC E 5 and PEG 6000 seal coat solution with the Opadry seal coat solution. The change to Example 1 was used to achieve a formulation with an 43 wt % taste-mask coat and 45 wt % drug load. This formulation was dissolution tested as described in Example 1. The details of the formulation are presented in Table 8, and dissolution data is presented in FIG. 8.

TABLE 8

| | Taste-mask coated formulation (43 wt % taste-mask coat, 45 wt % drug load) | |
|---|---|---|
| Layer | Ingredient | mg/g |
| Seed core | Microcrystalline cellulose pellets | 49.3 |
| Drug layer | Sodium phenylbutyrate | 450.6 |
| | HPMC E 5 | 45.1 |
| | PEG 6000 | 4.5 |
| | (H2O) | — |
| Seal coat | HPMC E 5 | 19.6 |
| | PEG 6000 | 2.4 |
| | (H2O) | — |
| Taste-mask coat | Eudragit E PO | 285.7 |
| | PEG 6000 | 28.5 |
| | Talc | 114.3 |
| | (acetone) | — |
| | (isopropyl alcohol) | — |

Example 8. Reconstitution with Dosing Vehicle and Administration

A formulation of sodium phenylbutyrate, e.g., the formulation prepared in Examples 1-7, can be suspension in water with the aid of a dosing vehicle for oral administration. The dosing vehicle is first prepared by adding 2.5 tsp of THICK-IT® to 120 mL of water and agitating. To this dosing vehicle are added 10 g of the taste-masked formulation, the mixture is agitated to suspend the beads, and the entire prepared dose is swallowed by the patient. The container is rinsed twice to ensure all of the taste-masked formulation is administered by adding an additional 120 mL of water, agitating to suspend any remaining formulation, and then swallowing; this process is repeated for a total of two rinses.

Example 9. Determination of Flavor Profile

A formulation of sodium phenylbutyrate, e.g., the formulation prepared in Examples 1-7, can be tested for palatability using any appropriate taste test known in the art, for example by a flavor profile test. The flavor profile method uses trained evaluators, such as a panel of 1, 2, 3, 4, 5, 6, 7, 8, 9, 10 or more experts, to identify, characterize, and quantify the perceived sensory attributes of a formulation.

Attributes identified by the panel are basic tastes (sweet, sour, salty, bitter, umami), aromatics (flavoring aromatics and aromatic "off-notes"), feeling factors (cooling, numbing, bite/burn, etc.), and amplitude (perception of balance and fullness). The perceived strength or intensity of each of these attributes will be measured and assigned an appropriate value: 0 for none, 1 for slight, 2 for moderate, and 3 for strong. Chemical reference standards are used to establish the intensity scale for on-going panelist calibration. Additionally, all sensations remaining in the aftertaste are measured at selected intervals over 1, 5, 10, 15 or more minutes.

Example 10. Determination of Distribution of Sodium Phenylbutyrate in Plasma

A Phase 1, single-center, single-dose, randomized, open-label, 4-sequence, 2-period, crossover study designed may be used to evaluate the bioequivalence of a taste-masked sodium phenylbutyrate formulation to BUPHENYL® in healthy male and female volunteers in fed and fasted states. Male and female volunteers are randomized to one of the 4 sequences to determine treatment for each study period. There is a minimum 12-hour washout between periods. The washout duration is regarded as sufficient as compared with the 0.8 hour mean terminal half-life reported for sodium phenylbutyrate in healthy adults At least 64 volunteers are enrolled in the study, with 16 randomized to each of the study sequences. An informed consent form is signed before any study-related procedures are performed. Treatments will be balanced for male and female volunteers.

The four treatment sequences are as follows in Table 9:

TABLE 9

| Treatment Sequences for Bioequivalence Study | | |
|---|---|---|
| Sequence | Period 1 | Period 2 |
| A | sodium phenylbutyrate fed | Taste-masked fed |
| B | Taste-masked fed | sodium phenylbutyrate fed |
| C | sodium phenylbutyrate fasted | Taste-masked fasted |
| D | Taste-masked fasted | sodium phenylbutyrate fasted |

Volunteers check into the study center at least 8 hours prior to Period 1 (Day-1) and remain at the study center for the 2 consecutive treatment periods, including remaining at the study center during the washout between Period 1 and Period 2 (Day 2). For fasted sequences, volunteers are required to fast for a minimum of 8 hours prior to initiating treatment (BUPHENYL® or the taste-masked formulation of sodium phenylbutyrate administration) for each period. For fed sequences, volunteers consume a United States Food and Drug Administration (FDA) standard high calorie, high fat breakfast beginning 30 minutes prior to administration of a composition prior in each period. Volunteers receive oral doses of 500 mg taste-masked formulation (per FDA Draft Guidance on Sodium Phenylbutyrate bioequivalence; May 2009). At each dosing time, the formulation is dissolved in 6 ounces of room temperature tap water by mixing gently. Volunteers are instructed to ingest the solution immediately.

Each treatment period lasts for 1 day. Blood draw schedules facilitate measurement of plasma phenylbutyrate levels at baseline and postdose for each period, and results are used to estimate the non-compartmental pharmacokinetic (PK) parameters. Blood samples for measurement of plasma concentrations of phenylbutyrate and phenylbutyrate metabolites are obtained in each study period at predose and at 0.25, 0.5, 0.75, 1.0, 1.5, 2.0, 2.5, 3.0, 4.0, and 8.0 hours postdose. The concentration of phenylbutyrate and phenylbutyrate metabolites in blood samples are measured using a validated liquid chromatography-tandem mass spectroscopy (LC-MS/MS) method. Blood samples may be stored for PK analyses for up to 12 months after the end of the study.

90% bioequivalence intervals are built comparing phenylbutyrate and phenylbutyrate metabolites in volunteers receiving either the taste-masked formulation or BUPHENYL® in fed (Sequences A and B) and fasted (Sequences C and D) states.

Safety is evaluated on the basis of incidence of adverse events and clinically significant changes in laboratory test results (chemistry, hematology, and urinalysis).

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. A pharmaceutical composition for oral administration of sodium phenylbutyrate comprising a plurality of layered particles having a volume-based particle size distribution in which at least 90% of the layered particles in the plurality of layered particles are smaller than 500 μm, wherein the layered particles comprise (i) a seed core; (ii) a drug layer comprising sodium phenylbutyrate; and (iii) a taste-mask coating comprising a polymer formed from dimethylaminoethyl methacrylate, butyl methacrylate, and methyl methacrylate, wherein the pharmaceutical composition comprises about 10 to 20% by total weight of the seed core, greater than 60% by total weight sodium phenylbutyrate, and about 5% to 25% by total weight taste-mask coating.

2. The pharmaceutical composition of claim 1, wherein the taste-mask coating is about 5 to 10% of the total weight.

3. The pharmaceutical composition of claim 1, wherein the sodium phenylbutyrate comprises about 65% of the total weight.

4. The pharmaceutical composition of claim 1, wherein the drug layer comprises sodium phenylbutyrate, a binder, and a plasticizer.

5. The pharmaceutical composition of claim 4, wherein the binder is hydroxypropyl methylcellulose.

6. The pharmaceutical composition of claim 4, wherein the plasticizer is polyethylene glycol having a molecular weight between 5,000 and 7,000.

7. The pharmaceutical composition of claim 1, wherein the drug layer comprises about 65% by total weight sodium phenylbutyrate; 5 to 7% by total weight hydroxypropyl methylcellulose; and 0.1 to 1% by total weight polyethylene glycol having a molecular weight between 5,000 and 7,000.

8. The pharmaceutical composition of claim 1, wherein the taste-mask coating further comprises a plasticizer and talc.

9. The pharmaceutical composition of claim 8, wherein the plasticizer is polyethylene glycol having a molecular weight between 5,000 and 7,000.

10. The pharmaceutical composition of claim 1, wherein the seed core comprises microcrystalline cellulose.

11. The pharmaceutical composition of claim 1, further comprising about 8 to 10% by total weight hydroxypropyl methylcellulose.

12. The pharmaceutical composition of claim 1, further comprising about 0.5 to 3% by total weight polyethylene glycol having a molecular weight between 5,000 and 7,000.

13. The pharmaceutical composition of claim 1, wherein the taste-mask coating further comprises talc, and wherein the talc is less than about 4% by total weight.

14. The pharmaceutical composition of claim 1, further comprising a seal coating between the drug layer and taste-mask coating.

15. The pharmaceutical composition of claim 14, wherein the seal coating comprises about 1 to 5% by total weight of the composition.

16. The pharmaceutical composition of claim 14, wherein the seal coating comprises a water soluble polymer.

17. The pharmaceutical composition of claim 1, wherein the pharmaceutical composition comprises about 65% by total weight sodium phenylbutyrate, 8 to 10% by total weight hydroxypropyl methylcellulose, 0.5 to 3% by total weight polyethylene glycol having a molecular weight between 5,000 and 7,000, 10 to 20% by total weight microcrystalline cellulose in the seed core, less than 4% by total weight of talc in the taste-mask coating, and 5 to 10% by total weight of the polymer formed from dimethylaminoethyl methacrylate, butyl methacrylate, and methyl methacrylate.

18. The pharmaceutical composition of claim 1, further comprising a glidant.

19. The pharmaceutical composition of claim 18, wherein the glidant is silica.

20. The pharmaceutical composition of claim 1, wherein, upon administration to a subject, the composition is bioequivalent to a sodium phenylbutyrate formulation that does not comprise a taste-mask coating.

21. The pharmaceutical composition of claim 1, wherein the plurality of layered particles has a volume-based particle size distribution in which at least 90% of the layered particles in the plurality of layered particles are smaller than about 400 μm.

22. The pharmaceutical composition of claim 1, formulated in unit dosage form.

23. The pharmaceutical composition of claim 1, wherein the composition scores favorably in a taste test in comparison to a sodium phenylbutyrate formation that does not comprise a taste-mask coating.

24. The pharmaceutical composition of claim 1, wherein, upon administration to a subject, the composition has greater sodium phenylbutyrate levels in the plasma at 30 minutes compared to a modified release formulation of sodium phenylbutyrate.

25. The pharmaceutical composition of claim 1, wherein less than 15% of the sodium phenylbutyrate in the composition dissolves in a neutral pH over a period of 10 minutes.

26. The pharmaceutical composition of claim 1, wherein at least 95% of the sodium phenylbutyrate in the composition dissolves at an acidic pH over a period of 60 minutes.

27. The pharmaceutical composition of claim 1, wherein the composition is a powder or granules.

* * * * *